United States Patent
Uchiyama et al.

(10) Patent No.: US 7,623,904 B2
(45) Date of Patent: Nov. 24, 2009

(54) MEDICAL APPARATUS, MEDICAL APPARATUS GUIDE SYSTEM, CAPSULE TYPE MEDICAL APPARATUS, AND CAPSULE TYPE MEDICAL APPARATUS GUIDE APPARATUS

(75) Inventors: Akio Uchiyama, Yokohama (JP); Hironao Kawano, Hachioji (JP); Takeshi Yokoi, Hino (JP); Kenichi Arai, Shiogama (JP); Kazushi Ishiyama, Sendai (JP); Masahiko Sendoh, Sendai (JP)

(73) Assignee: Olympus Corporation, Tokyo (JP)

( * ) Notice: Subject to any disclaimer, the term of this patent is extended or adjusted under 35 U.S.C. 154(b) by 516 days.

(21) Appl. No.: 10/910,738

(22) Filed: Aug. 3, 2004

(65) Prior Publication Data
US 2005/0085696 A1 Apr. 21, 2005

(30) Foreign Application Priority Data
Aug. 6, 2003 (JP) ............................. 2003-288273
Aug. 11, 2003 (JP) ............................. 2003-291771

(51) Int. Cl.
*A61B 5/05* (2006.01)
(52) U.S. Cl. ..................... 600/424; 600/101; 600/407; 600/423
(58) Field of Classification Search ................ 600/407, 600/423, 424, 101
See application file for complete search history.

(56) References Cited
U.S. PATENT DOCUMENTS
5,484,440 A * 1/1996 Allard .......................... 606/73
5,681,260 A * 10/1997 Ueda et al. ................ 600/114
2003/0020810 A1 * 1/2003 Takizawa et al. ............. 348/68

FOREIGN PATENT DOCUMENTS

| JP | 4-008343 | 1/1992 |
|---|---|---|
| JP | 6-063045 | 3/1994 |
| JP | 3075191 | 11/2000 |
| JP | 2001-179700 | 7/2001 |
| JP | 2002-000556 | 1/2002 |
| JP | 2002-187100 | 7/2002 |
| JP | 2002-214560 | 7/2002 |
| JP | 2002-307396 | 10/2002 |
| JP | 2002-360508 | 12/2002 |
| JP | 2003-38424 | 2/2003 |
| WO | WO 03/028224 A2 | 4/2003 |

* cited by examiner

*Primary Examiner*—Brian Casler
*Assistant Examiner*—James Kish
(74) *Attorney, Agent, or Firm*—Scully, Scott, Murphy & Presser, P.C.

(57) ABSTRACT

In a capsule 3 as a medical apparatus inserted into a body cavity, the lengthwise direction of the capsule 3 is used as an insert axis, a manipulation/input device 8, which is magnetized in a direction orthogonal to the insert axis, is disposed at the center position of the insert axis. A magnetic field generation device 4, which is disposed outside of a body, is caused to generate a vibration magnetic field in a direction parallel with the insert axis of the capsule 3 by turning on a vibration (ON/OFF) switch 8*f* of a manipulation/input device 8 so that couples having lines of action, which are in parallel with the insert axis, are exerted on the capsule 3, thereby the capsule 3 executes a swiveling motion about the insert axis and smoothly travels along a cavity organ.

20 Claims, 23 Drawing Sheets fr = fm fr = fm/2

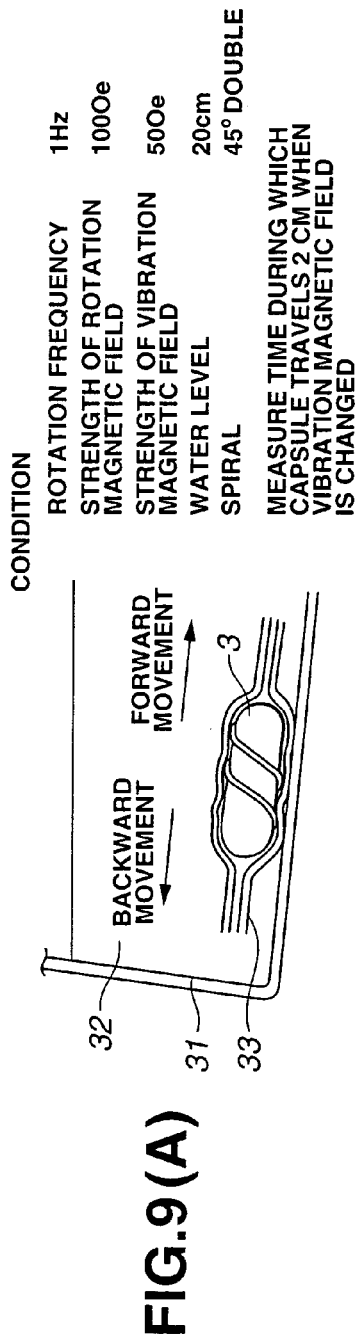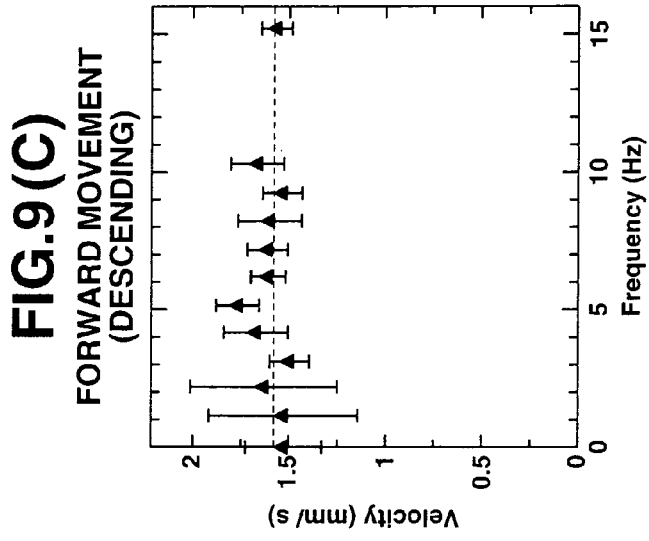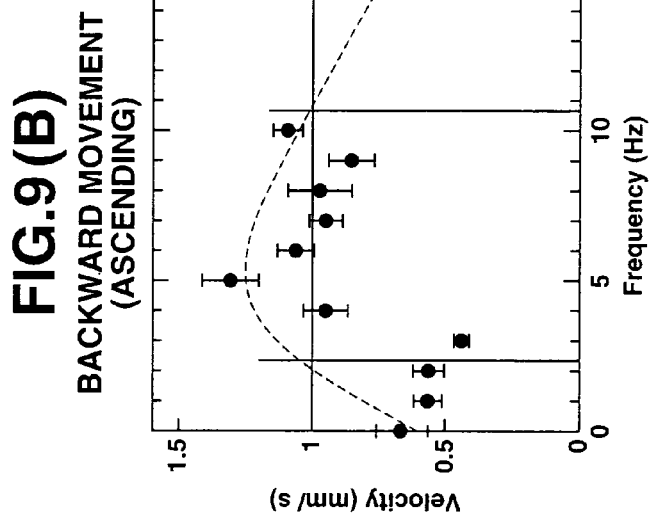

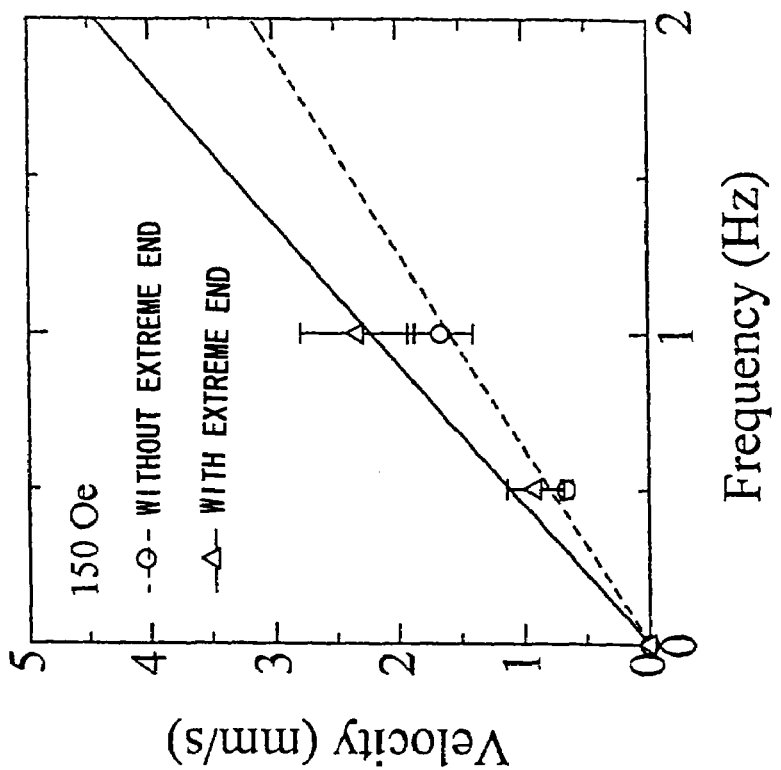
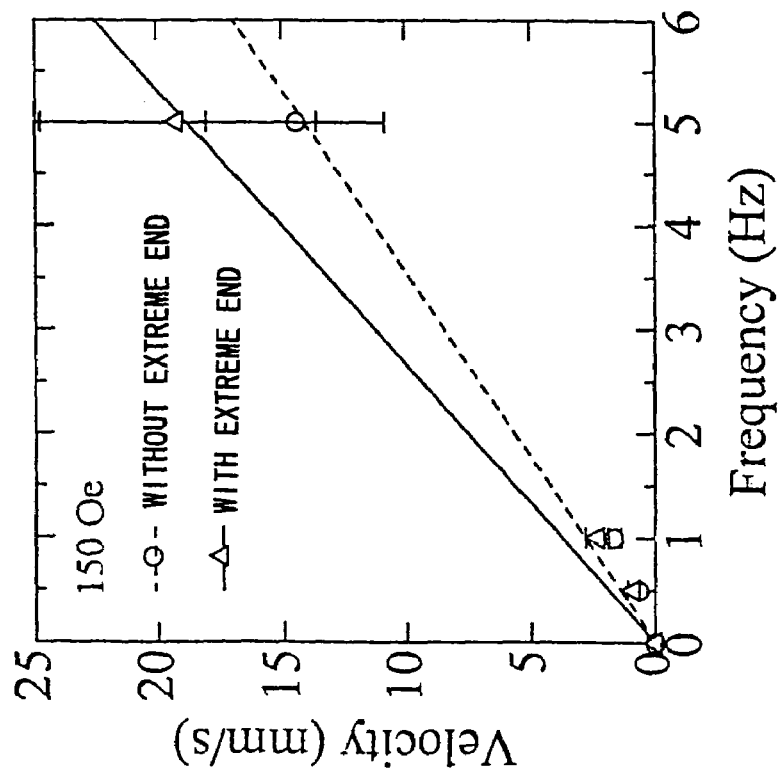

CONSTANT PITCH  a = b = c

MEDICAL APPARATUS, MEDICAL APPARATUS GUIDE SYSTEM, CAPSULE TYPE MEDICAL APPARATUS, AND CAPSULE TYPE MEDICAL APPARATUS GUIDE APPARATUS

This Application claims the benefit of Japanese Patent Applications Nos. 2003-291771 and 2003-288273 filed in Japan on Aug. 11, 2003, and Aug. 6, 2003, respectively, the contents of which are incorporated by this reference.

BACKGROUND OF THE INVENTION

1. Field of the Invention

The present invention relates to a medical apparatus inserted into a body cavity, a medical apparatus guide system, which is preferable to thrust and guide the medical apparatus while rotating it, a capsule type medical apparatus, and a capsule type medical apparatus guide apparatus.

2. Related Art Statement

Conventional arts for thrusting a micro machine in a body to be examined by a rotation magnetic field are disclosed in Japanese Unexamined Patent Application Publication Nos. 2001-179700 and 2002-187100. These conventional arts disclose a movement control system for a movable micro machine including a magnetic field generation device for generating a rotation magnetic field, a robot main body for obtaining a thrust by being rotated in response to the rotation magnetic field, a position detection device for detecting the position of the robot main body, and magnetic field change means for changing the direction of the rotation magnetic field generated by the magnetic field generation unit to direct the robot main body toward a destination where it reaches based on the position of the robot main body detected by the position detection device.

SUMMARY OF THE INVENTION

A medical apparatus of the present invention includes a couple generation device for generating couples having lines of action parallel to an insert axis in a medical apparatus having an insert portion inserted into a body cavity.

A medical apparatus of the present invention includes a medical apparatus having an insert portion inserted into a body cavity having an approximately cylindrical outside shape, a spiral structure disposed around the side of the medical apparatus main body, a thrust generation mechanism having rotation drive means for rotating the spiral structure about the cylindrical axis of the medical apparatus main body and generating a thrust in the direction of the cylindrical axis, and couple generation means having lines of action in parallel with the cylindrical axis.

A medical apparatus guide system of the present invention for guiding a medical apparatus into a body cavity includes a rotation magnetic field, a magnetic field generation device for generating a magnetic field in a direction perpendicular to the rotation plane of the rotation magnetic field, a medical apparatus main body having an insert portion inserted into the body cavity, a thrust generation structure disposed to the medical apparatus main body, and a magnet disposed to the medical apparatus main body with a magnetic pole direction facing a direction substantially orthogonal to the thrust generating direction of the thrust generation structure.

A capsule type medical apparatus of the present invention includes a capsule type medical apparatus main body having an insert portion inserted into the body cavity, a thrust generation structure disposed to the medical apparatus main body, and a magnet disposed to the medical apparatus main body in the vicinity of the center in the thrust generating direction of the capsule medical apparatus main body with a magnetic pole direction facing a direction substantially orthogonal to the thrust generating direction of the thrust generation structure.

A medical apparatus of the present invention for executing a medical action such as an examination, a treatment, or the like in a cavity organ of a body to be examined is arranged such that a main body is composed of a rotation symmetrical member having a symmetrical axis in a traveling direction, at least one of the front portion or the rear portion in a traveling direction of the main body is composed of a diameter-reduced portion having a diameter reduced toward an end and an approximately hemispherical end shape, an electromagnetic field response portion is disposed in the main body so that it is acted by the rotation of an electromagnetic field applied from the outside of the body to be examined, and a spiral structure is disposed on the outside surface of the main body and converting the rotating motion generated by the electromagnetic field response portion into a thrust, wherein an end of the spiral structure is disposed to reach the vicinity of an end of the main body.

A medical apparatus guide system of the present invention includes a medical apparatus comprising a main body composed of a rotation symmetrical member having a symmetrical axis in a traveling direction, a diameter-reduced portion arranged to at least one of the front portion or the rear portion of the main body in a traveling direction and having an approximately hemispherical end shape whose diameter is reduced toward an end, an electromagnetic field response portion disposed in the main body and acted by the rotation of an electromagnetic field applied from the outside of the body to be examined, a spiral structure disposed on the outside surface of the main body and converting a rotating motion generated by the electromagnetic field response portion into a thrust, wherein an end of the spiral structure is disposed to reach the vicinity of an end of the main body, electromagnetic field generation means for generating an electromagnetic field acting on the electromagnetic field response portion disposed to the medical apparatus, and electromagnetic field control means for controlling the direction of the electromagnetic field generated by the electromagnetic field generation means, wherein the electromagnetic field generation means generates the electromagnetic field in three-axis directions and rotates the medical apparatus in a cavity organ.

BRIEF DESCRIPTION OF THE DRAWINGS

FIG. 8(A) is a view showing a locus when the frequency of the rotation magnetic field is set equal to that of the vibration magnetic field, and the like;

FIGS. 9(A), 9(B), and 9(C) are views showing a result of measurement of a thrust velocity when the rotation magnetic field and the vibration magnetic field are applied using a sample;

FIGS. 29(A) and 29(B) are graphs showing a result of measurement of the thrust velocity;

DETAILED DESCRIPTION OF PREFERRED EMBODIMENTS

Embodiments of the present invention will be explained below with reference to the drawings.

First Embodiment

Figure 1:
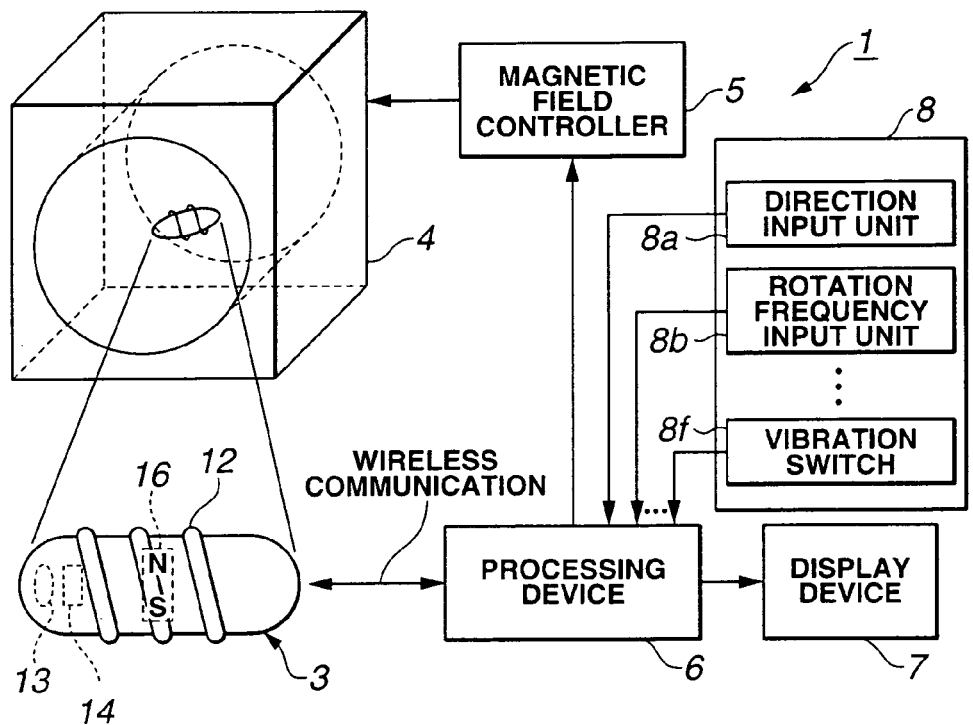
FIG. 1 is a schematic configurational view of a capsule type medical apparatus guide system having a first embodiment of the present invention, the configurational view mainly showing a rotation magnetic field generation device in particular.
Figure 5:
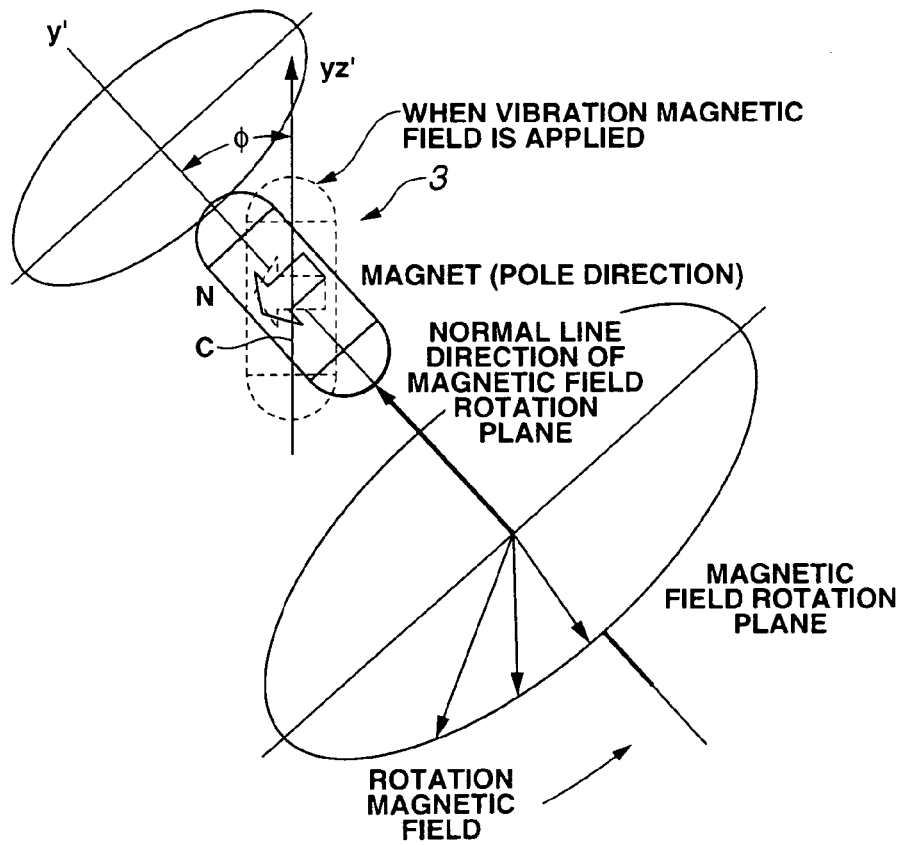
FIG. 5 is an explanatory view showing how a rotation magnetic field changes, and the like when it is applied.
Figure 2:
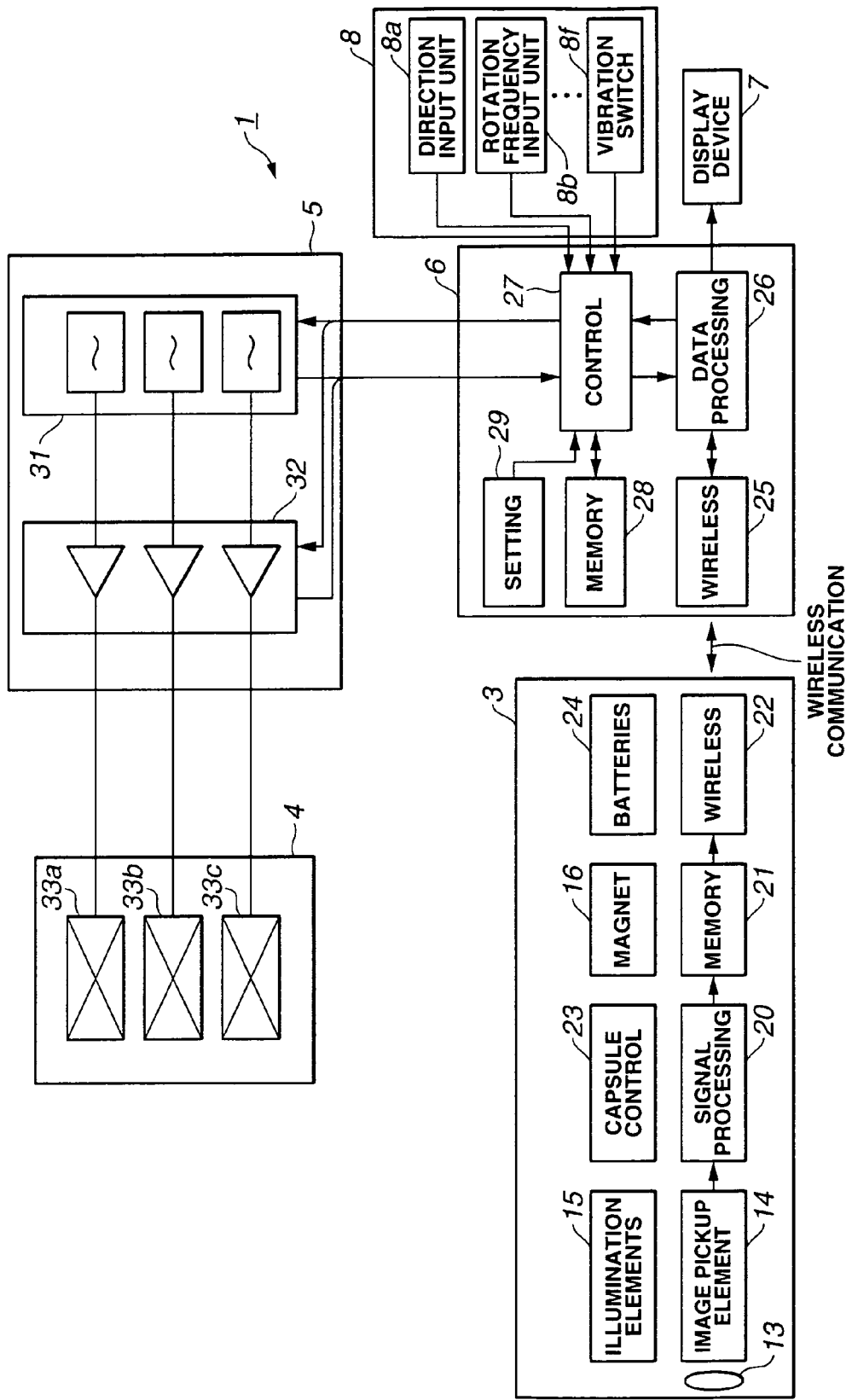
FIG. 2 is a block diagram showing the internal arrangements of respective portions in the capsule type medical apparatus guide system having the first embodiment of the present invention.
Figure 3:
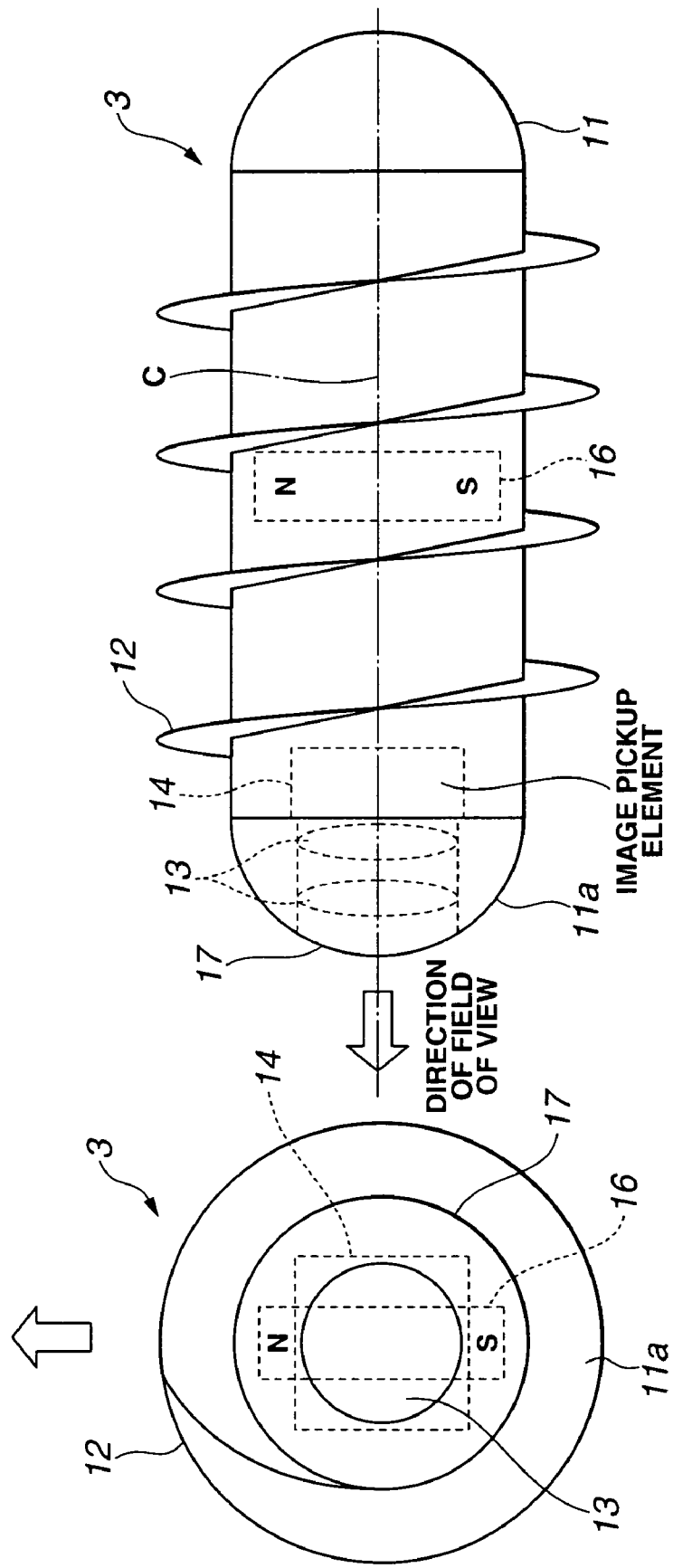
FIG. 3(A) is a side elevational view of a capsule main body.
FIG. 3(B) is a front elevational view of the capsule main body.
Figure 4:
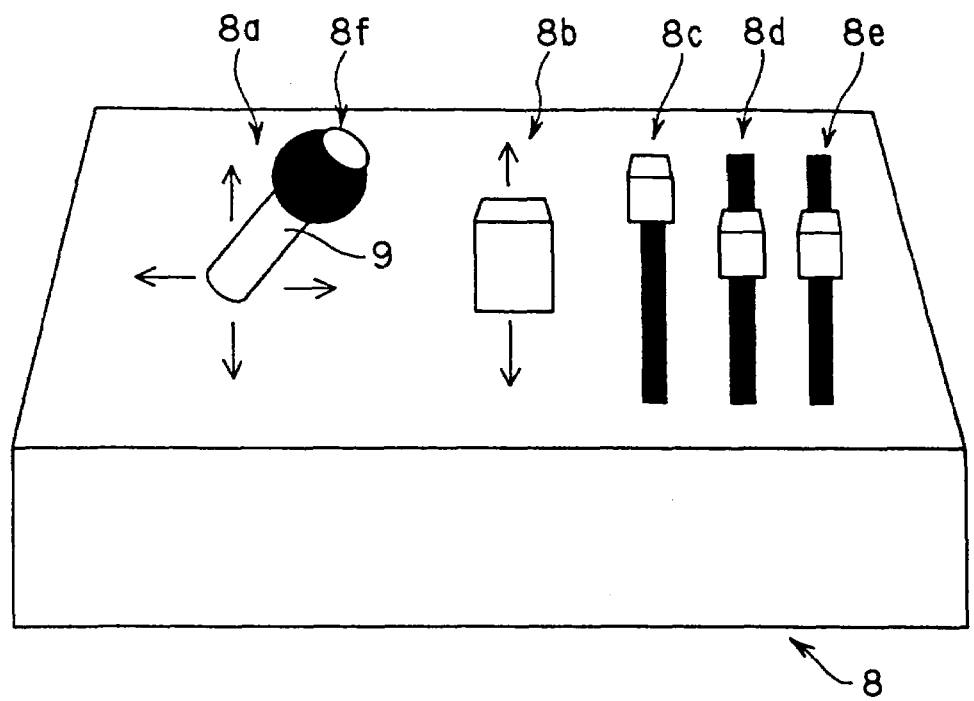
FIG. 4(A) is an explanatory view showing the arrangement of a manipulation/input device.
FIG. 4(B) is a view showing an image display screen for displaying information corresponding to the manipulation of the manipulation/input device shown in FIG. 4(A)
Figure 4:
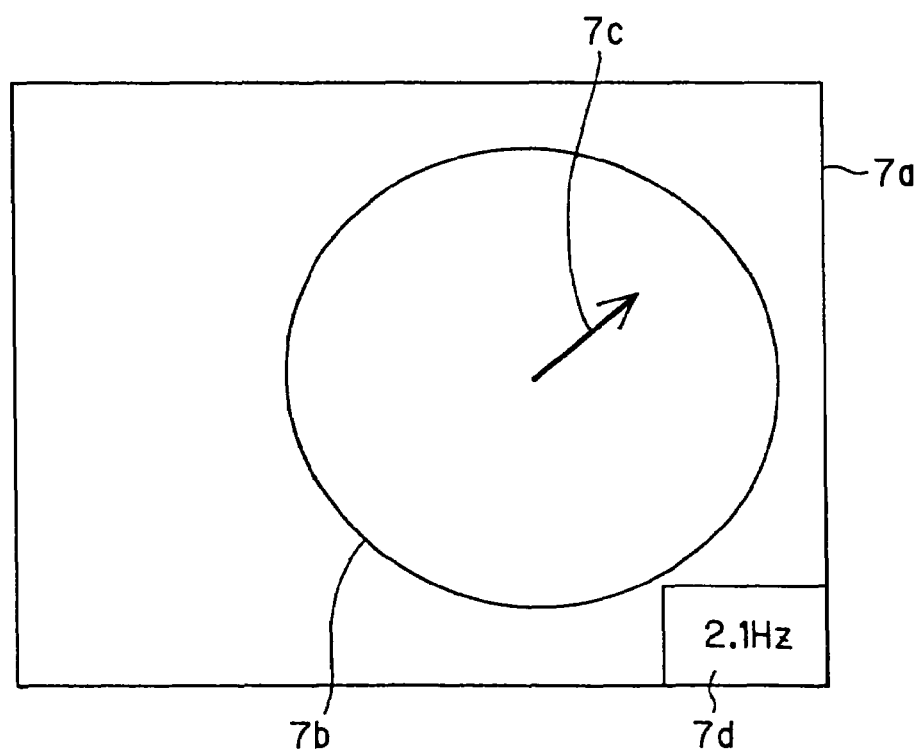
Figure 6A:
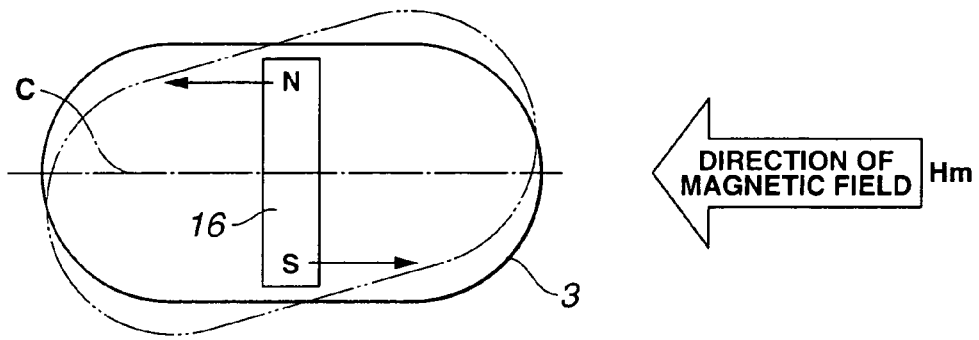
FIGS. 6(A) and 6(B) are schematic views showing the behavior of couples received by the capsule type medical apparatus when a vibration magnetic field is applied.
Figure 6B:
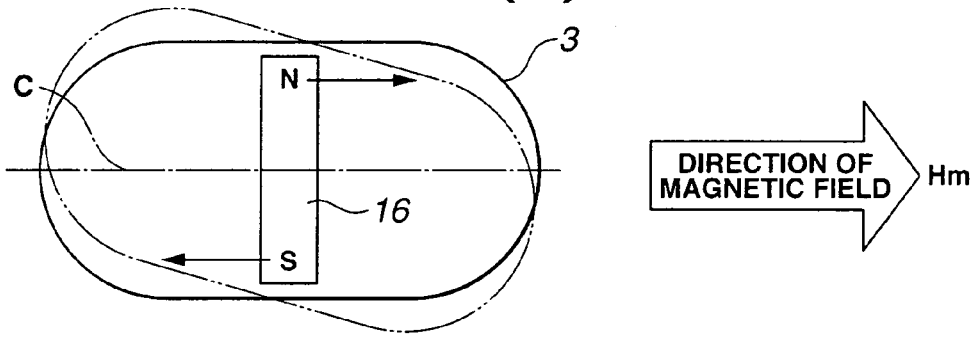
Figure 7A:
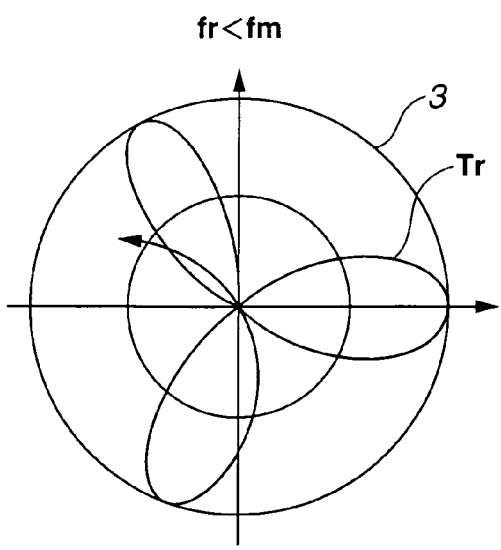
FIGS. 7(A) and 7(B) are views showing loci drawn by the extreme end of the capsule type medical apparatus when the frequencies and strengths of the rotation magnetic field and the vibration magnetic field are changed.
Figure 7B:
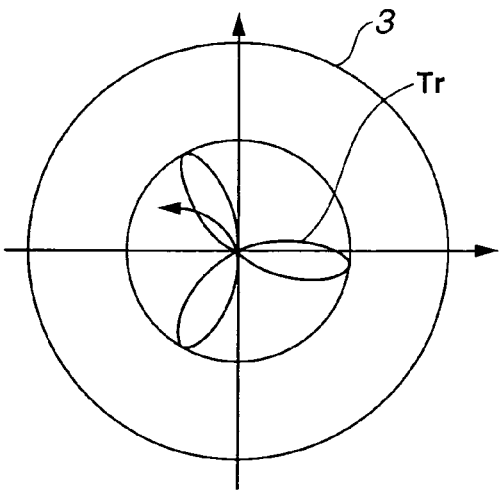
Figure 8A:
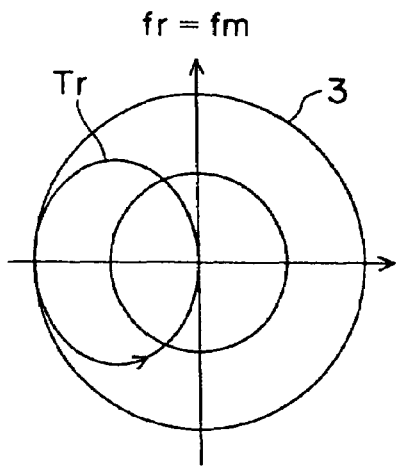
Figure 8B:
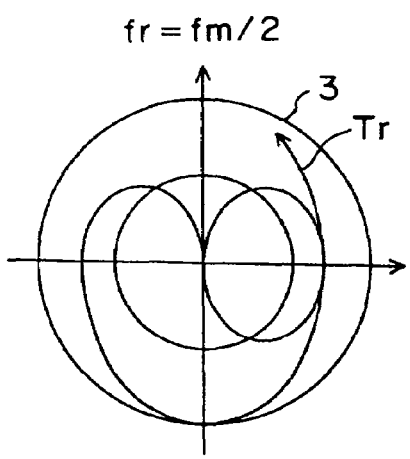
FIG. 8(B) is a view showing a locus drawn by the extreme end of the capsule type medical apparatus when the frequency of the vibration magnetic field is set twice that of the rotation magnetic field.
Figure 8C:
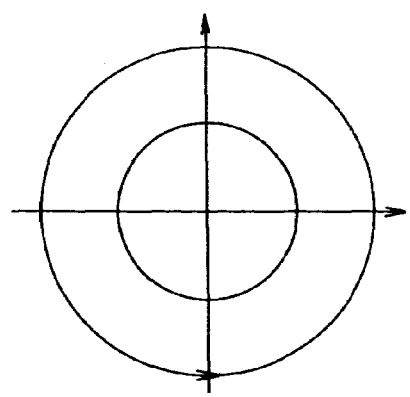
FIG. 8(C) is a view showing a locus drawn by the extreme end of the capsule type medical apparatus when a direct current is used in the vibration magnetic field.
Figure 10:
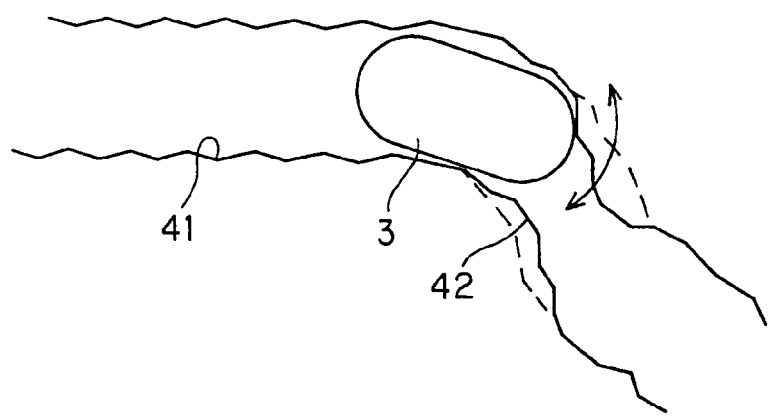
FIGS. 10(A), 10(B), 10(C), and 10(D) are explanatory views of motions of the capsule type medical apparatus when it thrusts in a curved cavity organ and a wide cavity organ.
Figure 10:
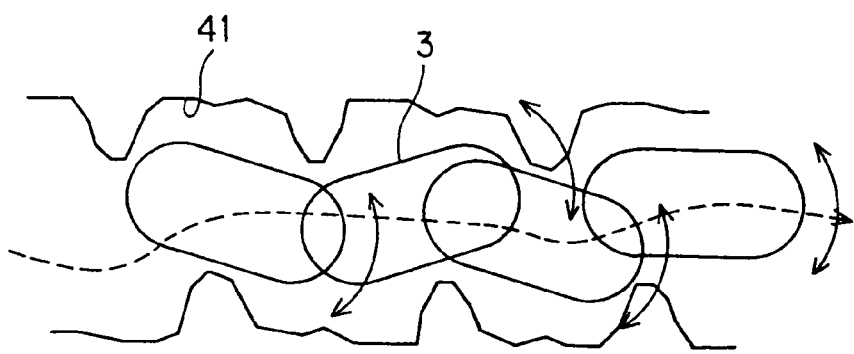
Figure 10:
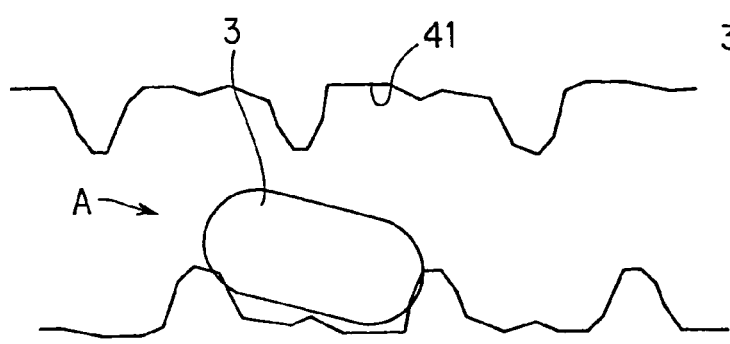
Figure 10:
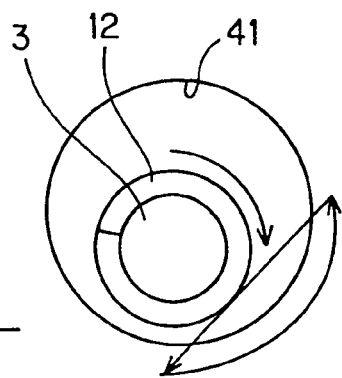
Figure 11:
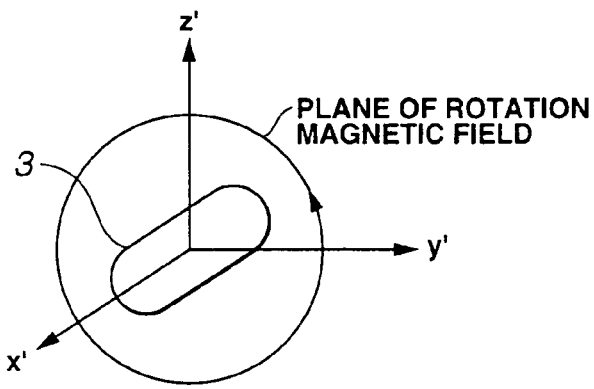
FIG. 11 is an explanatory view when the rotation magnetic field and the like are applied on a coordinate system on which the center axis of the capsule type medical apparatus is set in an x'-direction.
Figure 12:
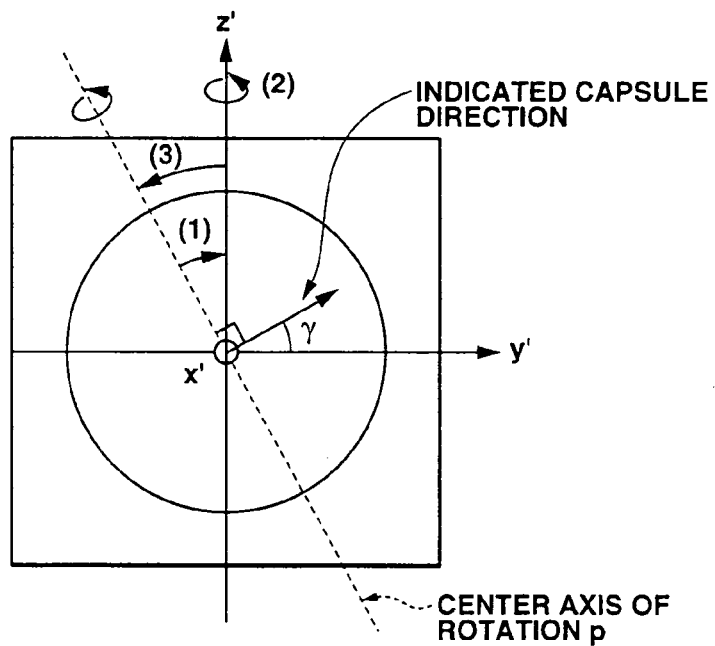
FIG. 12 is an explanatory view of calculation of the direction of a capsule and the direction of the rotation magnetic field when an indication for changing the direction of the capsule type medical apparatus is input.
Figure 13:
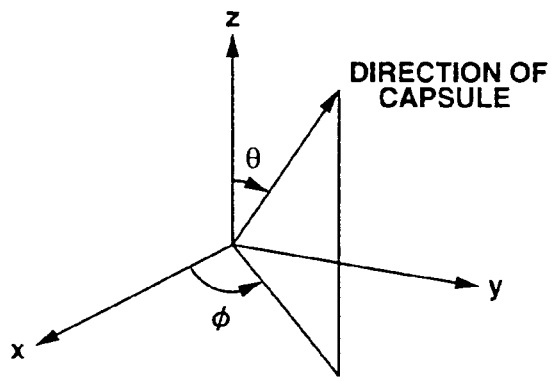
FIG. 13 is an explanatory view showing a new direction of the capsule type medical apparatus on a polar coordinate system.
Figure 14:
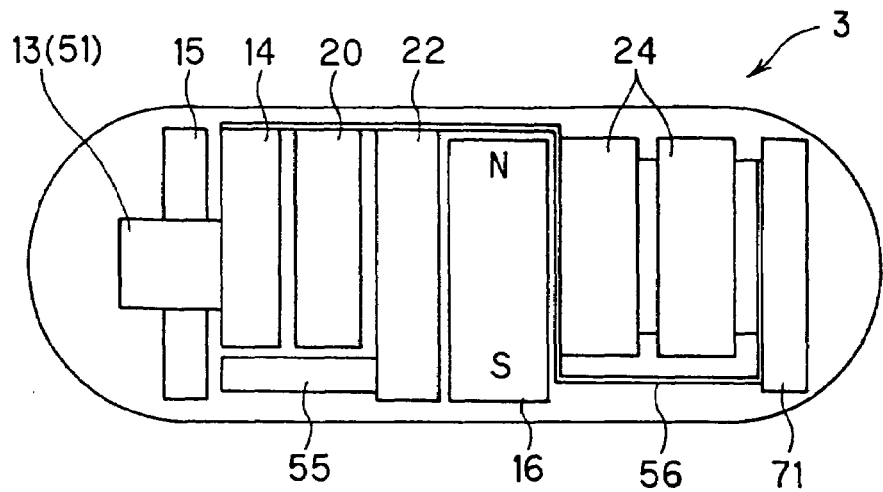
FIG. 14 shows a layout of the internal structure of the capsule type medical apparatus.
Figure 15:
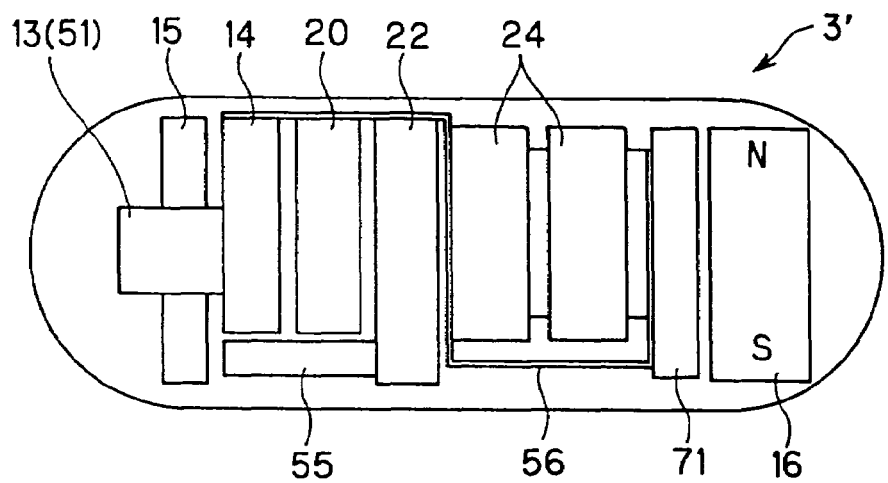
FIG. 15 shows a layout of a modification in which a magnet is disposed on the rear end side in FIG. 14.
Figure 16:
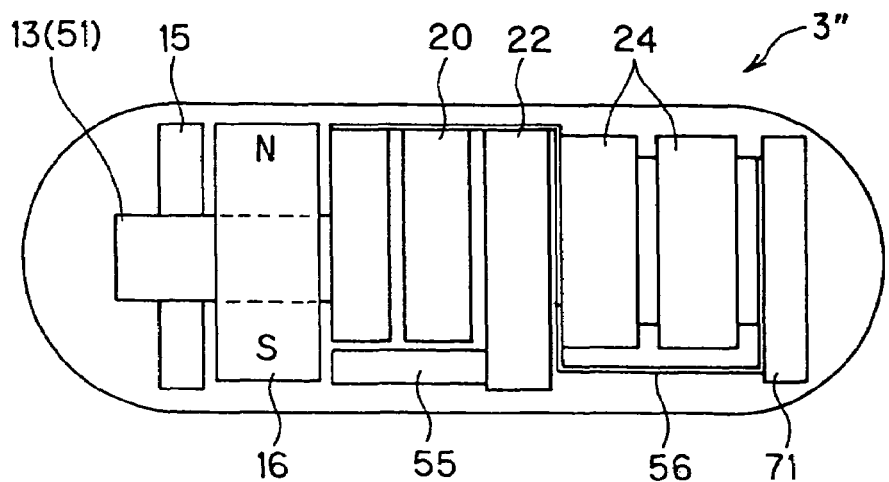
FIG. 16 shows a layout of a modification in which a magnet is disposed on an observation window side in FIG. 14.
Figure 17:
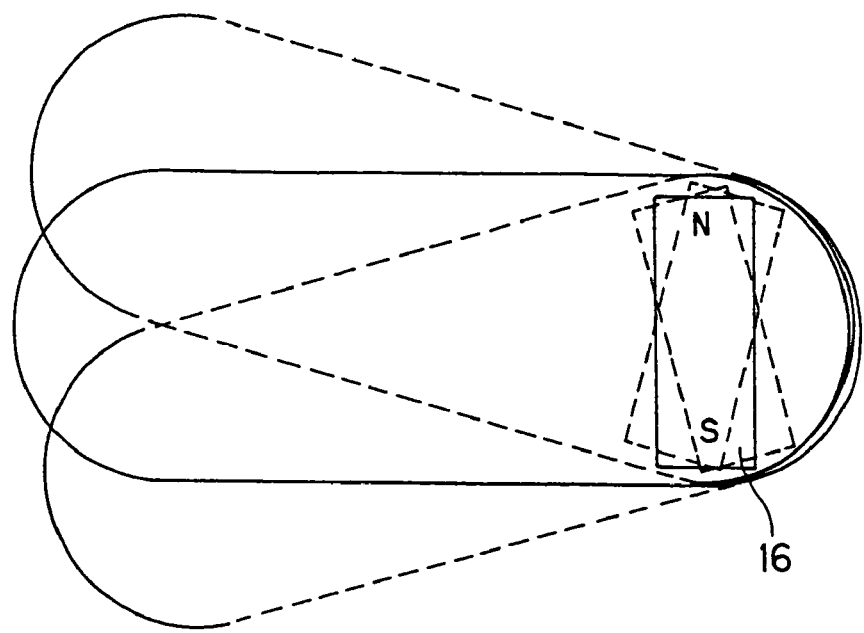
FIG. 17 is an explanatory view of an operation when the vibration magnetic field is applied to the layout shown in FIG. 15.
Figure 18A:
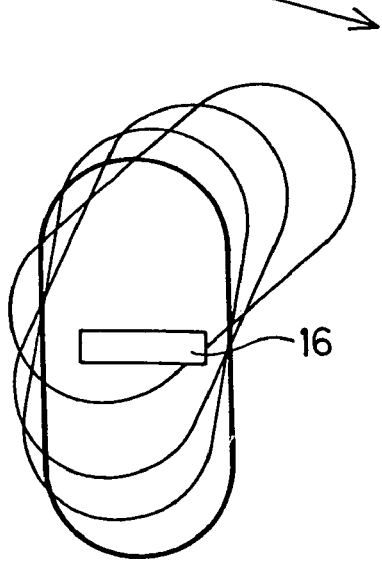
FIGS. 18(A) and 18(B) are explanatory views showing how the motion of the capsule is different when it is guided by the magnet disposed in the vicinity of the center of the capsule type medical apparatus main body and by the magnet disposed in the vicinity of an end thereof.
Figure 18B:
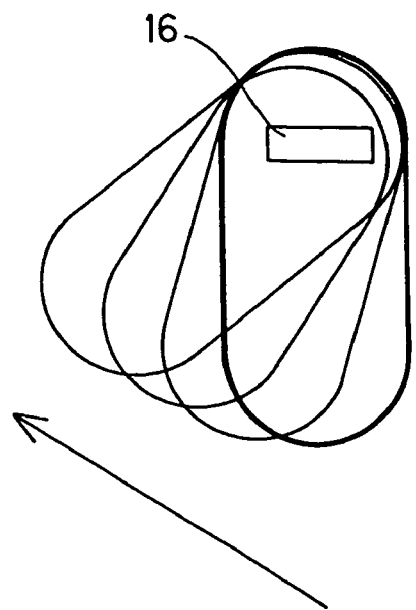

FIGS. 1 to 18 relate to a first embodiment of the present invention, in which FIGS. 1 and 2 show an overall arrangement of a capsule type medical apparatus guide system of a first embodiment; FIGS. 3(A) and 3(B) show a side elevational view and a front elevational view of a capsule main body; FIGS. 4(A) and 4(B) show an image display screen showing an arrangement of an manipulation/input device and information corresponding to the manipulation thereof; FIG. 5 shows how a rotation magnetic field changes, and the like when it is applied; FIGS. 6(A) and 6(B) show the behavior of couples received by the capsule type medical apparatus when a vibration magnetic field is applied; FIGS. 7(A) and 7(B) show views showing loci drawn by the extreme end of the capsule type medical apparatus when the frequencies and strengths of the rotation magnetic field and the vibration magnetic field are changed; FIG. 8(A) is a view showing a locus when the frequency of the rotation magnetic field is set equal to that of the vibration magnetic field, and the like; FIG. 8(B) shows a locus drawn by the extreme end of the capsule type medical apparatus when the frequency of the vibration magnetic field is set twice that of the rotation magnetic field; FIG. 8(C) is a view showing a locus drawn by the extreme end of the capsule type medical apparatus when a direct current is used in the vibration magnetic field; FIGS. 9(A), 9(B) and 9(C) show a result of measurement and the like of a thrust velocity when the rotation magnetic field and the vibration magnetic field are applied using a sample; FIGS. 10(A) to 10(D) show a motion explanatory views when the capsule type medical apparatus thrusts in a curved cavity organ and a wide cavity organ; FIG. 11 shows an explanatory view when the rotation magnetic field and the like are applied on a coordinate system on which the center axis of the capsule type medical apparatus is set in an x'-direction; FIG. 12 is an explanatory view of calculation of the direction of a capsule and the direction of the rotation magnetic field when an indication for changing the direction of the capsule type medical apparatus is input; FIG. 13 shows an explanatory view showing a new direction of the capsule type medical apparatus on an absolute coordinate system; FIG. 14 shows a layout of an internal structure of the capsule type medical apparatus; FIG. 15 shows a layout of a modification in which a magnet is disposed on the rear end side in FIG. 14; FIG. 16 shows a layout of a modification in which a magnet is disposed on an observation window side in FIG. 14; FIG. 17 shows an explanatory view of an operation when the vibration magnetic field is applied to the layout shown in FIG. 15; and FIGS. 18(A) and 18(B) show explanatory views showing how the motion of the capsule is different when it is guided by the magnet disposed in the vicinity of the center of the capsule type medical apparatus main body and by the magnet disposed in the vicinity of an end thereof.

As shown in FIGS. 1 and 2, a capsule type medical apparatus guide system 1 of the first embodiment of the medical apparatus guide system of the present invention includes a capsule type medical apparatus 3 (hereinafter, abbreviated to as capsule), a magnetic field generation device 4, a magnetic field controller (or power supply controller) 5, a processing device 6 composed of a personal computer or the like, a display device 7, and a manipulation/input device 8. The capsule 3 is inserted (guided) into a body cavity of a not shown patient and acts as a capsule type endoscope for picking up the image of the inside of the body cavity; the magnetic field generation device 4 is disposed around the patient, that is, externally of the patient' body and applies a rotation magnetic field and a couple generating magnetic field (or vibration magnetic field) to the capsule 3; the magnetic field controller 5 controls the supply of a drive current which generates the rotation magnetic field and the couple generating magnetic field (or vibration magnetic field) to the magnetic field generation device 4; the processing device 6 is disposed externally of the patient' body, and executes image processing through a wireless communication with the capsule 3 as well as controls the direction, magnitude, and the like of the rotation magnetic field and the couple generating magnetic field (or vibration magnetic field) applied to the capsule 3 by controlling the magnetic field controller 5 according to a manipulation executed by a manipulator; the display device 7 is connected to the processing device 6 and displays an image and the like recorded by the capsule 3; and the manipulation/input device 8 is connected to the processing device 6 and manipulated by the manipulator such an operator and the like, and an indication signal corresponding to the manipulation is indicated and input through the manipulation/input device 8.

As shown in FIG. 4(A), the manipulation/input device 8 includes a direction input unit 8a through which a direction, in which the capsule 3 inserted into the body is intended to thrust, is input and indicated, a rotation frequency input unit 8b, a rotation magnetic field strength adjustment unit 8c, a vibration (couple generating) magnetic field strength adjustment unit 8d, a vibration (couple generating) magnetic field frequency adjustment unit 8e, and a vibration (or couple generating) ON/OFF switch (abbreviated as vibration switch) 8f. The rotation frequency input unit 8b generates a signal for indicating a rotation magnetic field having a rotation frequency corresponding to a manipulation; the rotation magnetic field strength adjustment unit 8c adjusts the strength of the rotation magnetic field; and the vibration switch 8f is disposed at, for example, an apex of a joy stick 9 that constitutes the direction input unit 8a and turns on and off the application of the vibration (or couple generating) magnetic field. Note that, in the following description, the vibration (or couple generating) magnetic field is described as a vibration magnetic field (in almost all the cases).

As shown in FIG. 3, the capsule 3 is formed in an approximately cylindrical shape or a capsule shape and composed of an exterior vessel 11 which also acts as an insert portion inserted into a body. The exterior vessel 11 has a spiral projection (or screw portion) 12 formed around the outer circumferential surface thereof, the spiral projection 12 acting as a thrust generating structural portion for converting a rotation into a thrust (thrust force).

The spiral projection 12 has a round sectional structure having an approximately hemispherical shape and the like and disposed around the outer circumferential surface of the exterior vessel 11 so that it is in smooth contact with the inside wall surface of the body.

Further, the capsule 3 accommodates an image pickup means in the inside thereof hermetically sealed by the exterior vessel 11, the image pickup means being composed of an objective lens 13 and an image pickup element 14 disposed at a focusing position of the objective lens 13. Further, the exterior vessel 11 accommodates therein a magnet (permanent magnet) 16, in addition to illumination elements 15 (refer to FIG. 2), which are necessary to execute picking up an image, and the like, the magnet 16 being used to more smoothly thrust the capsule 3.

As shown in FIGS. 3(A) and 3(B), the objective lens 13 is disposed inwardly of, for example, a hemispherical transparent extreme end cover 11a in the exterior vessel 11 with its optical axis in agreement with a center axis C which is said to act as an insert axis of the cylindrical capsule 3. As shown in FIG. 3(B), an observation window 17 is formed at a central portion of the extreme end cover 11a. Note that, although not shown in FIGS. 3(A) and 3(B), the illumination elements 15 are disposed around the objective lens 13.

Accordingly, in this case, the direction of the field of view of the objective lens 13 is in agreement with the optical axis direction of the objective lens 13, that is, in agreement with a direction along the cylindrical center axis C of the capsule 3.

Further, as shown in FIGS. 3(A) and 3(B), the magnet 16, which is disposed in the vicinity of the center of the capsule 3 in a lengthwise direction, is disposed such that an N-pole and an S-pole are disposed in a direction orthogonal to the center axis C. In this case, the magnet 16 is disposed with its center in agreement with the position of the center of gravity of the capsule 3. Accordingly, when a magnetic field is applied from the outside, the center of a magnetic force acting on the magnet 16 agrees with the position of the center of gravity of the capsule 3 so that the capsule 3 can be smoothly thrust -17 magnetically.

Further, as shown in FIG. 3(B), the magnet 16 is disposed such that the magnetized direction thereof, that is, the direction of an electric dipole agrees with the specific direction in which the image pickup element 14 is disposed.

That is, an up-direction when an image recorded by the image pickup element 14 is displayed is set in a direction from the S-pole to the N-pole of the magnet.

Then, the magnet 16 is magnetically rotated by applying the rotation magnetic field to the capsule 3 by the magnetic field generation device 4 to thereby rotate the capsule 3 having the magnet 16 fixed therein together with the magnet 16. At the time, the spiral projection 12 formed on the outer circumferential surface of the capsule 3 is rotated in contact with the inner wall of the body cavity so that the capsule 3 can be thrust.

Further, FIGS. 6(A) and 6(B) schematically show a fundamental function (action) of the embodiment. As shown in the figures, the magnetic field generation device 4 can apply a vibration magnetic field (couple generating magnetic field) Hm whose magnetic field direction changes in the center axis C direction of the capsule 3 thereto (by turning on the vibration switch 8f). It is a feature of the invention that forces, which are parallel to the center axis C as shown by arrows in FIGS. 6(A) and 6(B) and have the same magnitude in an opposite direction (that is, couples) can be exerted on the magnet 16 built in the capsule 3.

In this case, the couples are parallel with the center axis C at respective points of both the magnetic poles of the magnet 16 on a line connecting them, have the same magnitude of forces in an opposite direction, and are exerted so as to rotate the capsule 3.

In the embodiment, the couples are exerted to the magnet 16 by the magnetic field applied from the outside. However, as explained in a second embodiment and the like to be described below, the capsule 3 may have such a structure that an inclining (swinging) mechanism causes the direction of the lengthwise insert axis of the capsule 3 to make vibration, inclination or the like so that the capsule 3 swivels and that pseud-couple generating means changes the position of a center of gravity (so that a force which corresponds one of couples is generated or exerted).

Further, in the embodiment, when the capsule having the magnet 16 built therein is controlled by an external magnetic field, the direction, to which the upper direction of the image recorded by the capsule 3 faces, can be found from the direction of the external magnetic field.

As shown in FIG. 2, accommodated in the capsule 3 are a signal processing circuit 20, a memory 21, a wireless circuit 22, a capsule control circuit 23, and batteries 24, in addition to the objective lens 13, the image pickup element 14, and the illumination elements 15, and the magnet 16 which are described above. The signal processing circuit 20 subjects a signal recorded by the image pickup element 14 to signal processing; the memory 21 temporarily stores a digital video signal created by the signal processing circuit 20; the wireless circuit 22 modulates the video signal read out from the memory 21 with a high frequency signal and converts it into a signal which is transmitted by wireless, modulates the control signal transmitted from the processing device 6, and so on; the capsule control circuit 23 controls the capsule 3 such as the signal processing circuit 20 and the like; and the batteries 24 supply an operation power to electric systems in the capsule 3 such as the signal processing circuit 20 and the like.

Further, the processing device 6, which makes a wireless communication with the capsule 3, includes a wireless circuit 25, a data processing circuit 26, a control circuit 27, and a memory circuit 28. The wireless circuit 25 makes a wireless communication with the wireless circuit 22, the data processing circuit 26 is connected to the wireless circuit 25 and subjects the image data sent from the capsule 3 to data processing such as image display processing and the like; the control circuit 27 controls the data processing circuit 26, the power supply controller 5 and the like; and the memory circuit 28 stores the information of the state of the rotation magnetic field generated by the magnetic field generation device 4 through the power supply controller 5 and the information set by the direction input unit 8a and the like.

The display device 7 is connected to the data processing circuit 26, and the image, which is recorded by the image pickup element 14 and processed by the data processing circuit 26 through the wireless circuits 22 and 25, and the like are displayed thereon. Further, since images are recorded by the capsule 3 while it is being rotated, the data processing circuit 26 executes image processing for correcting the directions of the images to be displayed on the display device 7 to a predetermined direction so that the operator can observe the images easily (described in Japanese Patent Application No. 2002-105493).

Indication signals corresponding to a manipulation are input to the control circuit 27 from the direction input unit 8a, the rotation frequency input unit 8b, and the like which constitute the manipulation/input device 8, and the control circuit 27 executes a control operation corresponding to the indication signals.

Further, the control circuit 27 is connected to the memory circuit 28 so that the memory circuit 28 stores the information of direction of the rotation magnetic field and the information of direction of the magnetic field at all times, these rotation magnetic field and the magnetic field being generated by the magnetic field generation device 4 through the magnetic field controller 5. Then, when a manipulation for changing the direction of the rotation magnetic field and the direction of the magnetic field is executed thereafter, the control circuit 27 can continuously change the direction of the rotation magnetic field and the direction of the magnetic field so that they can be smoothly changed. Note that the memory circuit 28 may be disposed in the inside of the control circuit 27.

Further, the magnetic field controller 5 connected to the control circuit 27 includes an alternate current generator/controller 31 and a driver portion 32. The alternate current generator/controller 31 is composed of three alternate current generation/control circuits for generating alternate currents as well as controlling the frequencies and phases of the alternate currents; and the driver portion 32 is composed of three drivers for amplifying the respective alternate currents, respectively. The currents output from the three drivers are supplied to three electromagnets 33a, 33b, 33c that constitute the magnetic field generation device 4, respectively.

In this case, the electromagnets 33a, 33b, 33c are disposed such that they generate magnetic fields in the three-axis directions that are orthogonal to each other. Contemplated as an example of the magnetic field generation device 4 is a three-axis Helmholtz coil in which the respective electromagnets 33a are composed Helmholtz coils and the directions of the magnetic fields generated thereby are orthogonal to each other.

Then, a signal for indicating a magnetic field direction can be generated by manipulating the direction input unit 8a constituting the manipulation/input device 8 shown in FIG. 4(A). A signal for indicating a rotation magnetic field having a rotation frequency corresponding a manipulation can be generated by manipulating the rotation frequency input unit 8b. The (alternate current or periodic) vibration magnetic field, which are set by the vibration magnetic field strength adjustment unit 8d and the like, can be generated by manipulating the vibration switch 8f. Accordingly, there can be generated couples which rotate the lengthwise center axis C itself of the capsule 3 about the center point thereof with respect to the magnet 16 of the capsule 3. In this case, since an alternate current is periodically applied to change the direction of the vibration magnetic field (exerted as couples) to an inverse direction before the center axis C itself is perfectly rotated, the capsule 3 is inclined or vibrated.

Note that, in FIG. 4(A), when the joy stick 9 in the direction input unit 8a is inclined in a direction in which the capsule 3 is desired to move, a rotation magnetic field, which moves the capsule 3 in the desired direction, is generated.

FIG. 5 shows the behavior of the capsule 3 when, for example, the rotation magnetic field is applied. The magnet 16 built in the capsule 3 can be rotated by applying the rotation magnetic field to the capsule 3, and the capsule 3 can be moved forward and backward by the rotation of the magnet 16.

Then, as shown in FIG. 5, a rotation magnetic field is applied to the capsule 3 such that a pole whose direction changes on the plane of the rotation magnetic field perpendicular to the direction (y' in FIG. 5) of the lengthwise center axis C of the capsule 3. The capsule 3 is rotated about the lengthwise direction thereof together with the magnet 16 fixed in the capsule 3 in a direction perpendicular to the lengthwise direction. Therefore, the capsule 3 can be engaged with the inside wall of the body cavity through the spiral projection 12 shown in FIG. 3 according to the rotational direction of the magnet 16 and moved forward or backward.

Further, in the embodiment, a vibration magnetic field (couple generating magnetic field) can be applied to the capsule 3, the vibration magnetic field acting to swing (vibrate) the magnet 16 about the direction y' of the lengthwise center axis C in FIG. 5. When the vibration magnetic field is applied, the lengthwise direction can be changed (vibrated) from the state shown by a solid line to the state shown by, for example, a dotted line (the direction of the center axis is shown by yz').

With the above operation, the capsule 3 is rotated about the lengthwise center axis C as well as decentered so that the direction of the center axis C of rotation of the capsule 3 inclines. That is, the capsule 3 can be placed in a state as if the rotation torque of a rotating top is reduced and the axle of the top is swung by the action of gravity (hereinafter, this motion will be called a zigzag motion).

With the above motion, when the capsule 3 is moved forward or backward in a body cavity having approximately the same diameter as that of the capsule 3 along the lengthwise direction of the body cavity, the capsule 3 can be smoothly moved by applying a rotation magnetic field which rotates the capsule 3 about the lengthwise direction thereof.

In contrast, when the capsule 3 is simply rotated about the lengthwise direction and comes into contact with a curved portion of a body cavity (refer to FIG. 10(A)), the capsule 3 may not be smoothly moved in a curved direction.

In this case, the capsule 3 is caused to execute the zigzag motion by applying a vibration magnetic field thereto so that a force is exerted on the capsule 3 to rotate the lengthwise center axis C of the capsule 3 along the axis about the center thereof as described above. With this operation, when the lengthwise direction is in agreement with the curved direction of the body cavity while the zigzag motion is being executed, the capsule 3 can be smoothly moved in the curved direction (which will be described later with reference to FIG. 10(A)).

Note that the state of the capsule 3 or the state of the rotation magnetic field are always grasped so that the direction of the rotation magnetic field can be controlled in any arbitrary desired direction from a present traveling direction by inclining the joy stick 9. In the embodiment, the state of the rotation magnetic field (specifically, the direction of the rotation magnetic field and the direction of a magnetic field) is stored in the memory circuit 28 at all times.

Specifically, the indication signal of the manipulation in the manipulation/input device 8 shown in FIG. 2 is input to the control circuit 27. The control circuit 27 outputs a control signal for generating a rotation magnetic field corresponding to the indication signal to the magnetic field controller 5 as well as stores the information of the direction of the rotation magnetic field and the direction of the magnetic field in the memory circuit 28.

Accordingly, the memory circuit 28 always stores the information of the direction of the rotation magnetic field generated by the magnetic field generation device 4 and the information of the direction of the magnetic field that changes periodically to form the rotation magnetic field.

Note that the memory circuit 28 is not limited to the case that it stores the information corresponding to the control signal of the direction of the rotation magnetic field and the direction of the magnetic field from the control circuit 27. That is, the information for determining the directions of the rotation magnetic field and the magnetic field, which are actually output to the magnetic field generation device 4 through the alternate current generator/controller 31 and the driver portion 32 in the magnetic field controller 5 in response to the control signal output from the control circuit 27 to the magnetic field controller 5, may be sent to the control circuit 27 from the magnetic field controller 5 side and stored in the memory circuit 28.

Further, in the embodiment, when the application of the rotation magnetic field begins and stops, and when the direction and the like of the rotation magnetic field (in other words, the traveling direction of the capsule) are changed, the rotation magnetic field is controlled to continuously change so that a force is not abruptly exerted but smoothly exerted on the capsule 3.

Further, in the embodiment, the images recorded by the image pickup element 14 are also rotated by the rotation of the capsule 3. When the images are displayed on the display device 7 as they are, the rotating images are also displayed, which deteriorates the manipulating property of the direction input unit 8a for indicating a desired direction and makes a manipulation to the desired direction. Thus, it is desired to stop the rotation of the displayed images.

Accordingly, in the embodiment, the data processing circuit 26 and the control circuit 27 execute processing for correcting the rotating images to images whose rotation is stopped as explained in Japanese Patent Application No. 2002-105493.

Note that an image may displayed by rotating it based on the information of a magnetic field direction so that the rotation of the capsule 3 is canceled (otherwise, a still image may be displayed in a predetermined direction by executing image correlation processing and the like).

Then, as shown in FIG. 4(B), a still image recorded by the image pickup element 14 is displayed in, for example, a circular display area 7b in a display screen 7a of the display device 7 as well as a manipulating direction of the joy stick 9 is shown by an arrow 7c, and an amount of manipulation of the joy stick 9 is shown by the size of the arrow 7c. Further, forward traveling/backward traveling is shown by a color of the arrow 7c.

Further, a frequency of the rotation magnetic field is displayed in a rotation magnetic field frequency display area 7d at, for example, a lower corner of the display screen 7a.

First, typical actions of the rotation magnetic field and the vibration magnetic field, which are features of the embodiment arranged as described above, will be explained.

FIGS. 6(A) and 6(B) show a state that a vibration magnetic field Hm is applied. In FIG. 6(A), the vibration magnetic field Hm causes couples to be exerted as shown by a line of action shown by an arrow, the couples rotating the magnet 16 fixed in the capsule 3 counterclockwise. The couples are exerted in a direction parallel to the center axis C of the capsule 3.

The capsule 3 receives forces (couples) from the vibration magnetic field Hm, the couples rotating the capsule 3 in the direction shown by a two-dot-and-dash line from the state shown by a solid line.

Further, when a vibration magnetic field Hm having a direction opposite to that shown in FIG. 6(A) is generated, couples, which rotate the magnet 16 fixed in the inside of the capsule 3 clockwise, are exerted on the capsule 3 as shown by FIG. 6(B), thereby the capsule 3 is rotated in the direction shown by a two-dot-and-dash line from the state shown by a solid line.

Further, FIG. 7(A) shows a locus Tr of the capsule 3 when it is viewed from the extreme end surface side thereof in the state that a rotation magnetic field Hr and the vibration magnetic field Hm are applied, wherein the relation between the frequency fr of the rotation magnetic field Hr and the frequency fm of the vibration magnetic field Hm is set to fr<fm.

Further, FIG. 7(B) shows the locus Tr of the capsule 3 in the state that the strength of the vibration magnetic field Hm is set one half that of the rotation magnetic field Hr in FIG. 7(A). In FIG. 7(B), the angle, at which the capsule 3 swivels from the center of rotation, is reduced to one half that in FIG. 7(A).

Further, FIG. 8(A) shows the locus Tr of the capsule 3 when the frequency fr of the rotation magnetic field Hr is set equal to the frequency fm of the vibration magnetic field Hm, that is, fr=fm in FIG. 7(A).

Under the above condition, the capsule 3 is placed in such a moving state (locus Tr) that it swivels while decentering on one side (left side in FIG. 8(A)).

Accordingly, this is effective when it is desired to push and widen a body cavity to one side.

Further, FIG. 8(B) shows the locus Tr of the capsule 3 when the frequency fr of the rotation magnetic field Hr is set one half the frequency fm of the vibration magnetic field Hm, that is, fr=fm/2 in FIG. 7(A).

Further, the case that the vibration magnetic field Hm is periodically changed has been described above. However, in the case in which the vibration magnetic field Hm may be applied as a magnetic field that does not change (fm=0, Hm≠0), the locus Tr of the capsule 3 turns in the same frequency as that of the frequency fr of the rotation magnetic field Hr as shown in FIG. 8(C).

Further, as shown in FIG. 9(A), this embodiment creates a state simulating that the capsule 3 is inserted into the tube of a body cavity by filling a vessel 31 with water 32, and placing a silicon tube 33, into which the capsule 3 is inserted, on the bottom of the vessel 31.

Then, the vessel 31 is disposed in the magnetic field generation device 4 shown in FIG. 1, and a rotation magnetic field, which caused the silicon tube 33 to travel right (forward) and left (backward) in the lengthwise direction (right and left direction in FIG. 9(A)) of the silicon tube 33, is applied as well as a vibration magnetic field is applied after its frequency is changed. Then, a period of time during which the capsule 3 moved 2 cm is measured, and a moving velocity of the capsule 3 during the time is calculated.

In this case, the frequency of the rotation magnetic field is set to 1 Hz, the strength of the rotation magnetic field is set to 100 Oe, the strength of the vibration magnetic field is set to 50 Oe, a water level is set to 20 cm, and two spiral projections 12, which are formed on the capsule 3 at a forming angle of 45°, are employed. Further, in this embodiment, the moving velocity is calculated in the state that the silicon tube 33 is slightly inclined downward in a right direction (that is, the left side of the tube is raised). That is, forward traveling (descending) is executed in the right direction, and backward traveling (ascending) is executed in the left direction.

A result of measurement in the backward traveling is as shown in FIG. 9(B), and a result of measurement in the forward traveling is as shown in FIG. 9(C). From the results shown in FIGS. 9(B) and 9(C), it is effective to cause the capsule 3 to travel, in particular, backward in the ascending direction to make the frequency of the vibration magnetic field higher than that of the rotation magnetic field.

Further, under the condition of this embodiment, data shows that it is effective to a thrust velocity to set the frequency of the vibration magnetic field to about 2 to 10 Hz. Further, the data shows that it is effective to the thrust velocity to set the frequency of the vibration magnetic field to about 2 to 10 times that of the rotation magnetic field.

Next, an overall action of the embodiment will be explained.

When the inside of a body cavity is examined with the capsule 3, a patient swallows the capsule 3. When the capsule 3 inserted into the body cavity passes through an esophagus and the like, an image recorded by the image pickup element 14 while being illuminated with the illumination elements 15 is transmitted by wireless to the processing device 6 outside of a body through the wireless circuit 22.

The processing device 6 stores image data, which is received by the wireless circuit 25 and demodulated, in an image storing device (such as a hard disc or the like) disposed in the data processing circuit 26 and the like as well as subjects the image data to display processing and outputs it to the display device 7, thereby the images sequentially recorded by the capsule 3 are displayed thereon.

The operator can assume an approximate present position of the capsule 3 in the body cavity from the images displayed on the display device 7. When the operator determines that the esophagus, for example, is being recorded regardless of that a portion to be examined is, for example, a portion located on a deeper side such as an intestinum tenue and the like, it is preferable to move the capsule 3 more speedily through portions on the way. In this case, the direction (direction of a normal line) of the rotation magnetic field generated by the magnetic field generation device 4 is initially set on a lower side of the patient along his or her body height. Note that, the spiral projection 12 provided with the capsule 3 in this case is formed in, for example, a right screw state assuming that the direction of a field of view through which an image is recorded by the image pickup element 14 is a direction facing a front side.

When, for example, the direction input unit 8a and the like are initially manipulated to generate the rotation-magnetic field, the control circuit 27 starts a setting circuit 29 and displays an initial state setting screen on the display device 7 or the like so that the operator can select the direction of the rotation magnetic field generated in the initially set state. This is because that information corresponding to the state of the rotation magnetic field just before the initial manipulation of the direction input unit 8a and the like is not stored in the memory circuit 28. Then, the operator indicates to initially generate the rotation magnetic field in the direction on the lower side of the patient along his or her body height, thereby the initial generation information of the rotation magnetic field is stored in the memory circuit 28.

Further, it is also possible to set the magnitude (amplitude) of the rotation magnetic field by the setting circuit 29 so that a rotation magnetic field having a value exceeding the magnitude is not generated. The information set by the setting circuit 29 is stored in the memory circuit 28.

Then, the control circuit 27 reads out the information stored in the memory circuit 28 and controls the information to generate the rotation magnetic field such that the direction thereof is set on the lower side of the patient along his or her body height by inclining the joy stick 9 and the manipulation lever 8b of the manipulation/input device 8 shown in FIG. 4(A). That is, the rotation magnetic field is generated by the magnetic field generation device 4 through the magnetic field controller 5 based on the information read out from the memory circuit 28.

As described above, the rotation magnetic field is applied from the outside of the body, and a magnetic torque is exerted on the magnet 16 built in the capsule 3 inserted into the body cavity, and the capsule 3 is rotated. At the time, the capsule 3 is rotated as if a screw is rotated with the spiral projection 12 formed on the outer circumferential surface of the capsule 3 in contact with the inside wall of the body cavity, thereby the capsule 3 is thrust promptly.

Further, the information of the state of the rotation magnetic field (the direction of the rotation magnetic field and the direction of the magnetic field) is stored in the memory circuit 28 at all times, and the information of the state of the rotation magnetic field in the state that the application thereof is stopped is also stored in the memory circuit 28.

Then, when a manipulation for applying the rotation magnetic field is executed again, a rotation magnetic field similar to the case that the rotation magnetic field is stopped is generated based on the information stored in the memory circuit 28.

The capsule 3 can be thrust along the tract in the body cavity as described above. When, however, when a narrower curved portion 42 exists in a relatively narrow cavity 41 and is curved as shown in, for example, FIG. 10(A), it may be difficult to cause the capsule 3 to effectively travel along the curved portion 42 only by the rotation magnetic field.

In this case, the capsule 3 can be caused to make the zigzag motion while swiveling about the axis along the lengthwise direction thereof by applying a vibration magnetic field together with the rotation magnetic field as shown in FIG. 7(A) and the like so as to further exert couples on the capsule 3.

The cavity portion of the curved portion 42 is pressed and widened by the above swivel action as shown by a dotted line of FIG. 10(A) as well as the capsule 3 can be thrust in the curving direction of the curved portion 42 when it faces the curving direction.

Further, FIG. 10(B) shows an action when the capsule 3 is effectively thrust through a cavity 41 larger than the outside diameter of the capsule 3.

As shown in FIG. 10(B), when it is intended to thrust the capsule 3 through the cavity 41 larger than the outside diameter of the capsule 3, the simple application of the rotation magnetic field is liable to rotate the capsule 3 at idle, and thus the capsule 3 is liable to travel at a slow velocity. This is because (the spiral projection 12 formed around) the outer circumferential surface of the capsule 3 is engaged with the inside surface of the cavity 41 (portion to be caught) in a small portion as shown in FIG. 10(C) or 10(D).

Note that FIG. 10(D) shows the state of the capsule 3 when it is viewed in the direction of an arrow A in FIG. 10(C), and when the capsule 3 is simply rotated, the capsule 3 rotates with position thereof less changed, and a function of running idle is lowered.

In this case, the capsule 3 is caused to execute a swiveling motion as shown in FIG. 10(B) by applying the vibration magnetic field together with the rotation magnetic field as shown in FIG. 7(A) and the like so that the effective outside diameter of the capsule 3 is increased in the state of the swiveling motion as well as a traveling direction is periodically changed, thereby the capsule 3 can be effectively thrust even in the case of the wide cavity 41 by increasing the engaging portion of the capsule 3 with the inside wall of the cavity 41.

Further, it is possible to thrust the capsule 3 stably and effectively through the cavity 41 having an inside diameter larger than the outside diameter of the capsule 3 by causing the capsule 3 to execute the swiveling motion (zigzag motion) as shown in FIG. 10(B) as well as it is also possible to image the inside wall of the cavity 41 in a larger range by substantially increasing an imaging area by executing the zigzag motion.

Further, as described above, in the embodiment, the manipulating direction and the like of the joy stick 9 are shown by the arrow 7c as shown in FIG. 4(B) so that the traveling direction of the capsule 3 can be indicted in a recorded image. Then, the magnetic field generation device 4 generates a rotation magnetic field is generated so that the capsule 3 can travel in the indicated direction according to the direction.

The control circuit 27 executes processing for calculating the direction in which the rotation magnetic field is generated in this case, and the magnetic field generation device 4 generates the rotation magnetic field corresponding to the indicated direction through the magnetic field control circuit 5.

An operation for generating the rotation magnetic field in this case will be explained below in detail.

Here, a rotation magnetic field strength, a vibration magnetic field strength and the like, which depend on an input time t, are shown by Hr(t), Hm (t) and the like.

rotation magnetic field strength: Hr(t)→set by 8c
vibration magnetic field strength: Hm(t)→set by 8d
frequency of rotation magnetic field: fr(t)→set by 8b
frequency of vibration magnetic field: fm(t)→set by 8e
sampling cycle: Ts→time intervals at which the system switches a magnetic field strength or at which the input amounts of the joystick and the like are read
phase of present rotation: β(t)
phase of present couples: α(t)
parameter for determining an amount of change of direction: C
Vy'(t): input amount in y' direction of joystick 8a at time t
Vz'(t): input amount in z' direction of joystick 8a at time t FIG. 11 shows a coordinate system (x', y', z') on which the center axis direction of the capsule 3 is set to x'. In this coordinate system (x', y', z'), since the center axis direction of the capsule 3 is set to x', the capsule 3 is caused to travel in the direction of the center axis x' thereof, and the magnetic field is set as described below in the state the vibration magnetic field is applied in the direction of the center axis x'.

$$Hx'(t+Ts)=Hm(t)\cos(\alpha(t)+2\pi Tsfm(t))$$

$$Hy'(t+Ts)=Hr(t)\cos(\beta(t)+2\pi Tsfr(t))$$

$$Hz'(t+Ts)=Hr(t)\sin(\beta(t)+2\pi Tsfr(t))$$

Hy', Hz' show the rotation magnetic fields, and Hx' corresponds to the vibration magnetic field.

Here, the present phases within a trigonometric function are shown as follows and used below.

$$\alpha(t+Ts)=\alpha(t)+2\pi Tsfm(t)$$

$$\beta(t+Ts)=\beta(t)+2\pi Tsfr(t)$$

FIG. 12 shows an explanatory view of a calculation of a new direction of the capsule 3 when an indication of direction of the capsule 3 is input.

It is assumed in the state shown in FIG. 12 that a capsule direction (a direction covered by an angle between an y'-axis and an angle γ) is indicated to the capsule 3 (whose center axis direction is x') to change the traveling direction thereof as shown by an arrow.

In this case, when the coordinate system is rotated about a rotation center axis p perpendicular to the indicated capsule direction, the direction of a new x' axis is the direction of the rotation magnetic field. The calculation of the rotation is realized by the following processes.

(1) rotation of −γ about x' axis (arrow (1) in FIG. 12)
(2) rotation of δ about z' axis (arrow (2) in FIG. 12)
(3) rotation of γ about x' axis (arrow (3) in FIG. 12).

Here, δ shows the input amounts Vy'(t), Vz'(t) of the joy stick 9.

$$V(t) = ((Vy'(t)^2 + (Vz'(t))^2)^{1/2}$$

$$\delta(t) = C \times V(t)$$

$$\gamma = \sin^{-1}(Vz'(t)/V(t))$$

Accordingly, a transformation matrix in which δ(t) rotation is executed about the rotation center axis p is shown as follows using a rotation matrix $R_\gamma^{x'}$, $R_{\delta(t)}^{z'}$, $R_{-\gamma}^{x'}$ corresponding to the manipulations (1), (2), (3).

$$R_{\delta(t)}^{p} = R_\gamma^{x'} R_{\delta(t)}^{z'} R_{-\gamma}^{x'}$$

Here, Expressions 1 are shown as follows, and they are rotation matrixes about respective axes.

$$R_{\gamma(t)}^{x'} = \begin{pmatrix} 1 & 0 & 0 \\ 0 & \cos\gamma & -\sin\gamma \\ 0 & \sin\gamma & \cos\gamma \end{pmatrix}$$ (Expressions 1)

$$R_{\delta(t)}^{z'} = \begin{pmatrix} \cos\delta(t) & -\sin\delta(t) & 0 \\ \sin\delta(t) & \cos\delta(t) & 0 \\ 0 & 0 & 1 \end{pmatrix}$$

$$R_{-\gamma(t)}^{x'} = \begin{pmatrix} 1 & 0 & 0 \\ 0 & \cos\gamma & \sin\gamma \\ 0 & -\sin\gamma & \cos\gamma \end{pmatrix}$$

Accordingly, a magnetic field to be applied anew is shown by Expression 2 using these rotation matrixes.

$$\begin{pmatrix} Hx'(t+Ts) \\ Hy'(t+Ts) \\ Hz'(t+Ts) \end{pmatrix} = R_{\gamma(t)}^{x'} R_{\delta(t)}^{z'} R_{-\gamma(t)}^{x'} \begin{pmatrix} Hx'(t+Ts)|_{v(t)=0} \\ Hy'(t+Ts)|_{v(t)=0} \\ Hz'(t+Ts)|_{v(t)=0} \end{pmatrix}$$ (Expression 2)

However, $Hx'(t+Ts)|_{v(t)=0}$, $Hy'(t+Ts)|_{v(t)=0}$, $Hz'(t+Ts)|_{v(t)=0}$ shows the respective magnetic fields in x', y', Z' directions in t+Ts when V(t)=0.

In contrast, the magnetic fields generated by the three-axis Helmholtz coil at the time t are shown by (Hx(t) Hy(t) Hz(t)).

Further, when the direction of the capsule 3 is shown using φ(t), θ(t), it is as shown in FIG. 13. Further, when the magnetic field side is transformed from a coordinate system x', y', z' to the coordinate system x, y, z, it is shown by Expressions 3 at the time t+Ts.

$$\begin{pmatrix} Hx(t+Ts) \\ Hy(t+Ts) \\ Hz(t+Ts) \end{pmatrix} = R_{\phi(t)}^{z} R_{\theta(t)}^{y} \begin{pmatrix} Hx'(t+Ts) \\ Hy'(t+Ts) \\ Hz'(t+Ts) \end{pmatrix}$$ (Expression 3)

$$\begin{pmatrix} Hx(t+Ts) \\ Hy(t+Ts) \\ Hz(t+Ts) \end{pmatrix} = R_{\phi(t)}^{z} R_{\theta(t)}^{y} R_{\gamma(t)}^{x'} R_{\delta(t)}^{z'} R_{-\gamma(t)}^{x'} \begin{pmatrix} Hx'(t+Ts) \\ Hy'(t+Ts) \\ Hz'(t+Ts) \end{pmatrix}$$

where, $R_{\phi(t)}^{z}$, $R_{\theta(t)}^{y}$ in Expressions 3 show a rotation matrix corresponding to the rotating manipulation of the angle φ(t) about the z-axis of FIG. 13 and the angle θ(t) about the γ-axis.

The magnetic field generated from the outside can be calculated by repeating these calculations.

In general, since the magnetic field of a coil is shown as follows.

$$H = I \cdot N$$

where, H: magnetic field, N: coefficient, I: current Accordingly, the current I, that is, I=H/N is controlled.

When the coefficients of the three-axis Helmholtz coil are shown by Nx, Ny, Nz, respectively, currents Ix(t), Iy(t), Iz(t) that flow to the coils are shown by Expression 4.

$$\begin{pmatrix} Ix(t) \\ Iy(t) \\ Iz(t) \end{pmatrix} = \begin{pmatrix} Hx(t)/Nx \\ Hy(t)/Ny \\ Hz(t)/Nz \end{pmatrix}$$ (Expression 4)

As to the information of a capsule direction:

(1) when there is position direction detection means, θ(t), φ(t) are used based on a result of detection by the position detection means. NDI Aurora®, and the like can be used as the position direction detection means (sensor) at the time; and (2) when no position is detected, θ(0), φ(0) (initial values) are input.

The direction of the capsule 3 thereafter is determined by Expression 5, and the direction is defined as the direction of the capsule 3.

$$\begin{pmatrix} X(t+Ts) \\ Y(t+Ts) \\ Z(t+Ts) \end{pmatrix} = R_{\phi(t)}^{z} R_{\theta(t)}^{y} R_{\gamma(t)}^{x'} R_{\delta(t)}^{z'} R_{-\gamma(t)}^{x'} \begin{pmatrix} 1 \\ 0 \\ 0 \end{pmatrix}$$ (Expression 5)

Further, the capsule (medical apparatus) 3 shown in FIG. 3 has the magnet 16 disposed at a central portion of the capsule 3, the central portion acting as a medical apparatus main body of the capsule 3. FIG. 14 shows an internal layout view of the capsule 3.

The objective lens 13 attached to (an objective lens frame 51), the illumination elements 15, and the image pickup element 14 are disposed at the end of an observation window. Further, the signal processing circuit 20 (it is built in the memory 21 in this case) and the wireless circuit 22 are disposed, and the magnet 16 is disposed behind the wireless circuit 22. The batteries 24 and a switch circuit 71 are disposed on the opposite side of the observation window across the magnet 16. The respective units are wired through a flexible substrate 56 as wiring means, thereby the capsule type medical apparatus 3 is arranged to realize the motion described above. With the above layout, the magnet 16 can be disposed at the central portion of the capsule type medical apparatus 3. Further, in the above layout, the position of the magnet 16 is located near to the position of the center of gravity of the capsule type medical apparatus 3. With the above layout, the rotation drive force and the like of the capsule type medical apparatus 3 main body, which are generated by applying the magnetic field from the outside, are generated in the vicinity of the center of gravity thereof.

Accordingly, the capsule type medical apparatus 3 can be stably controlled.

However, in the following case, better controllability may be obtained by not disposing the magnet 16 in the vicinity of the center of the capsule type medical apparatus.

FIG. 15 shows a capsule 3' of a modification in which the location of the magnet 16 is changed with the location of the batteries 24 and the switch circuit 71 in FIG. 14 so that the magnet 16 is disposed at the end opposite to the observation window side.

The above arrangement is advantageous when the capsule 3' is guided into a relatively large cavity of a colon and the like.

When a motion shown in FIG. 18(B) is executed, if the magnet 16 is disposed in the vicinity of the capsule 3 as shown in FIG. 14, the capsule 3 main body is vibrated as shown in FIGS. 6(A) and 6(B) by the vibration magnetic field applied thereto.

In contrast, when the magnet 16 is disposed as shown in FIG. 15, the capsule 3 is vibrated by the vibration magnetic field applied thereto such that the amplitude of the end of the capsule main body, which is located on the observation window side, is increased as shown in FIG. 17. With the above motion, the portion, where the inside wall of a cavity is engaged with the capsule 3', can be secured (increased) even in a larger cavity.

Accordingly, the capsule 3' has an effect that it can be guided even into the larger cavity.

Further, in FIG. 16, the magnet 16 is arranged to have a hollow a structure, inserted into the objective lens frame 51, and fixed therein. With the above structure, the magnet 16 can be disposed in the vicinity of the end of a capsule 3" on the observation window side thereof.

How the capsule 3" of FIG. 16 executes a different motion when it is guided (to make a direction change motion) will be explained in comparison with the capsule 3 of FIG. 3 and FIG. 14.

As shown in FIG. 18(A), the capsule 3 of FIG. 3 or FIG. 14 executes a direction change motion about the vicinity of the center of the capsule 3 (the position of the magnet 16). Thus, when a cavity abruptly curves, there is a case that a turning-radius cannot be secured along the cavity and a guiding property is deteriorated.

In contrast, the capsule 3" of FIG. 16 acts as described below.

That is, since the capsule 3" changes its direction about the vicinity of the observation window as shown in FIG. 18(B), the turning-radius can be easily secured.

Accordingly, the capsule 3" has an effect that it can improve the guiding property.

According to the embodiment described above, even if a cavity, into which the capsule 3 and the like are desired to be inserted, is wider or narrower than the outside diameter of the capsule 3 and the like or curved, the capsule 3 and the like can smoothly pass therethrough, thereby the capsule 3 and the like can be guided to a target portion side in a short time.

Further, since the capsule 3 and the like can be moved in the cavity at a velocity higher than conventional arts, the capsule 3 and the like can be guided to the target portion side in a short time.

Second Embodiment

Figures 19A, 19B:
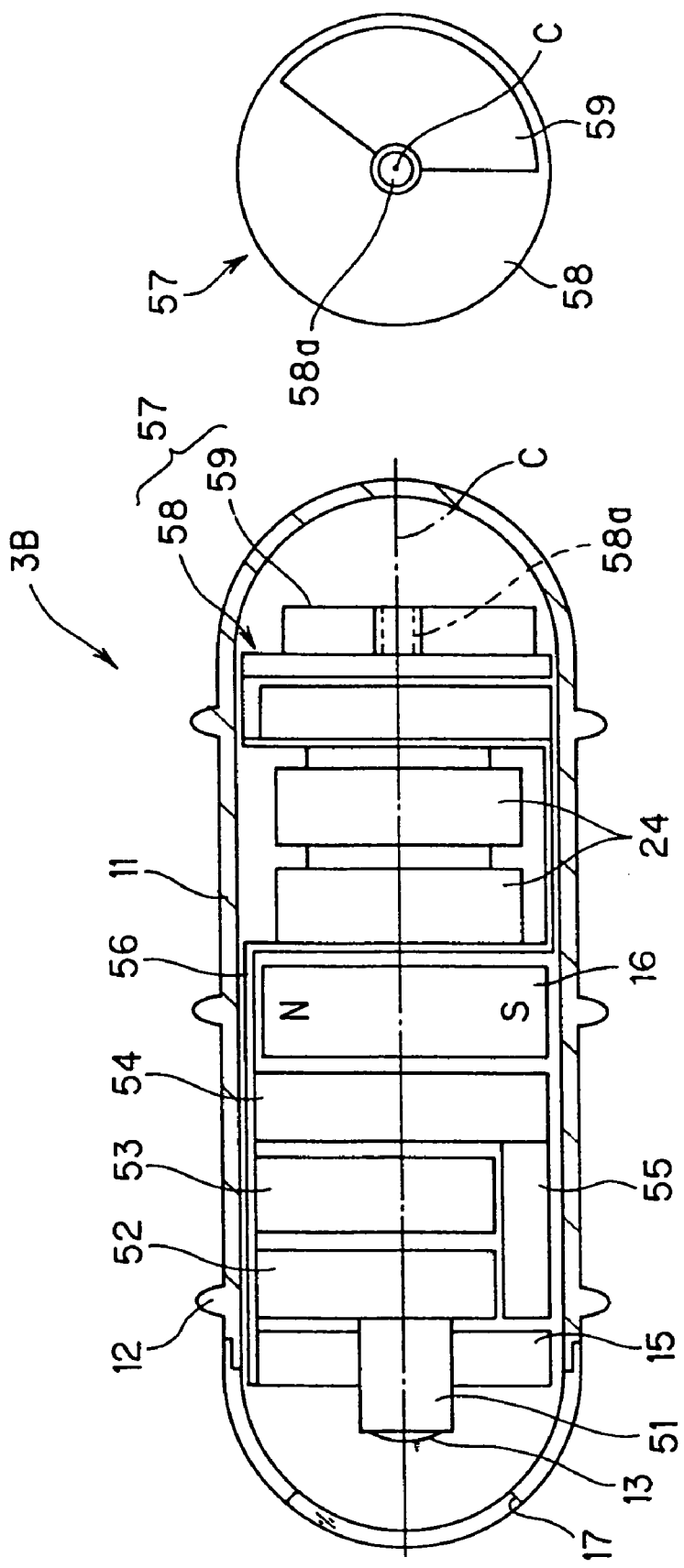
FIGS. 19(A) and 19(B) are views showing a capsule type medical apparatus and a pager motor of a second embodiment of the present invention.

Next, a second embodiment of the present invention will be explained with reference to FIG. 19. FIG. 19 shows a capsule 3B of the second embodiment of the present invention. FIG. 19(A) shows an inside arrangement of the capsule 3B, and FIG. 19(B) shows a pager motor 57 portion when it is observed from a rear end.

In the first embodiment, the magnet 16 is built in the capsule 3, and the rotation magnetic field is applied to the capsule 3 from the outside as well as the vibration magnetic field is applied thereto in a direction orthogonal to the rotation magnetic field. With this operation, couples are exerted on the capsule 3 so that it passively inclines its center axis C. In the present embodiment, however, an inclining force or a vibration force is exerted on the capsule 3B so that it actively inclines its center axis C.

The capsule 3B shown in FIG. 19 includes a spiral projection 12 formed on the outer circumferential surface of a capsule-like exterior vessel 11 likewise the capsule 3 of FIG. 3(A). Further, an observation window 17 formed of a transparent material is disposed to the exterior vessel 11 at an extreme end thereof.

A cylindrical objective lens frame 51 to which an objective lens 13 is attached is disposed in the inside of the capsule 3B in confrontation with the observation window 17, an image pickup element substrate 52 to which an image pickup element 14 is attached is disposed at the image pickup position of the objective lens 13, and illumination elements 15 are disposed around the objective lens frame 51.

A control substrate 53, which executes signal processing and control, and a communication substrate 54, which has functions of a wireless circuit 22 and the like, are disposed adjacent to the image pickup element substrate 52, and an antenna 55 is connected to the communication substrate 54. Further, the illumination elements 15, the image pickup element substrate 52, and the like are electrically connected through a flexible substrate 56.

A magnet 16 is disposed at a central position on the lengthwise center axis C of the capsule 3B such that the direction of the magnet 16 orthogonal to the center axis C becomes the lengthwise direction thereof and fixed by a not shown adhesive or the like.

Further, batteries 24 are accommodated adjacent to the magnet 16 and connected to the flexible substrate 56 through a not shown switch. Furthermore, the pager motor 57 is accommodated in an accommodating portion in the vicinity of the rear end of the capsule 3B adjacent to the batteries 24 and connected to a control substrate 53 and the like through the flexible substrate 56, the pager motor 57 being used to decenter or to vibrate so as to swivel the capsule 3B from the direction of the center axis C.

The pager motor 57 comprises, for example, an ultrasonic motor 58 and a weight 59 disposed to the ultrasonic motor 58.

As shown in FIG. 19(B), the ultrasonic motor 58 has a rotating shaft 58a to which the conical or fan-shaped weight 59 is attached. The weight 59 is rotated together with the rotation of a rotor side of the ultrasonic motor 58. With the above arrangement, a center of gravity position change mechanism is formed whose position of the center of gravity is changed depending on a position of the weight 59, thereby the capsule 3B executes a swiveling motion (vibrates) as the weight 59 rotates.

Further, the capsule 3B includes communication means to communicate with a processing device 6 outside of a body likewise the communication means explained in the first embodiment.

In the first embodiment, when the vibration switch 8f of the manipulation/input device 8 is turned on, the control circuit 27 in the processing device 6 controls the magnetic field generation device 4 so that it generates the vibration magnetic field. In the present embodiment, however, a control circuit 27 transmits its indication signal to the capsule 3B side through a wireless circuit 25.

When the capsule 3B receives the indication signal and decodes the command, a capsule control circuit 23 (refer to FIG. 2, the control substrate 53 in FIG. 19) operates the pager motor 57. Further, when a vibration switch 8f is turned off, the capsule 3B stops the operation of the pager motor 57. Note that a rotation magnetic field acts likewise the first embodiment.

An operation of the embodiment arranged as described above will be explained.

In the present embodiment, a manipulation for rotating the capsule 3B is the same as that of the first embodiment. Then, when it is desired for the capsule 3B to thrust through, for example, a curved cavity organ more smoothly, the vibration switch 8f provided with a manipulation/input device 8 is depressed as shown in FIG. 2. Thus, vibration-ON-information is transmitted to the wireless circuit 25 through the control circuit 27.

The vibration-ON-information is transmitted to the capsule 3B by a wireless communication. On receiving the signal, the capsule control circuit 23 of the capsule 3B turns on the rotation of the pager motor 57.

With this operation, the capsule 3B actively generates forces (pseudo-couples) for inclining or swinging it about its center axis C by pseudo-couples (that is, a force corresponding to one of forces for forming couples), thereby the capsule 3B can execute a vibrating motion or a swiveling motion. A method of obtaining a thrust by applying the rotation magnetic field is the same as the first embodiment.

Note that when a signal for indicating the number of rotation of the pager motor 57 is set by a wireless communication, the frequency of vibration can be changed.

According to the present embodiment, a simple manipulation can make the capsule 3B to execute the vibrating motion or the swiveling motion without applying a vibration magnetic field from the outside.

Further, the capsule 3B may be thrust while being rotated by the creeping motion of a cavity organ in a body through a spiral projection 43B disposed around the capsule 3B in the state that no rotation magnetic field is applied thereto. According to the present embodiment, the capsule 3B can be vibrated even in a small-scale system having no magnetic field generation device 4 for generating a rotation magnetic field, thereby the capsule 3B can smoothly pass through a curved portion.

Third Embodiment

Figure 20:
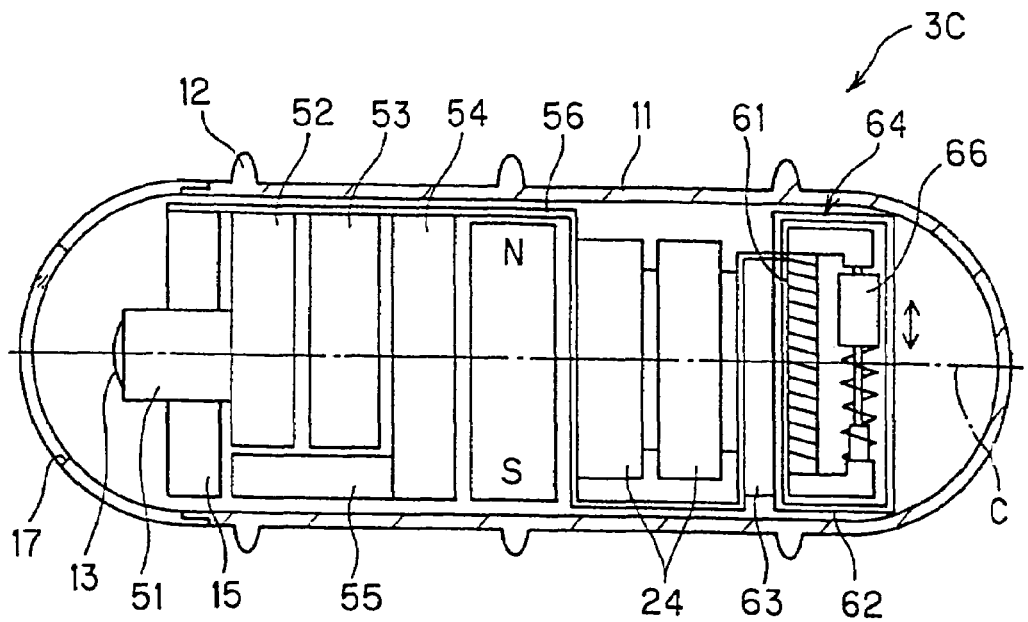
FIG. 20 is a sectional view showing a capsule type medical apparatus of a third embodiment of the present invention.
Figure 21A:
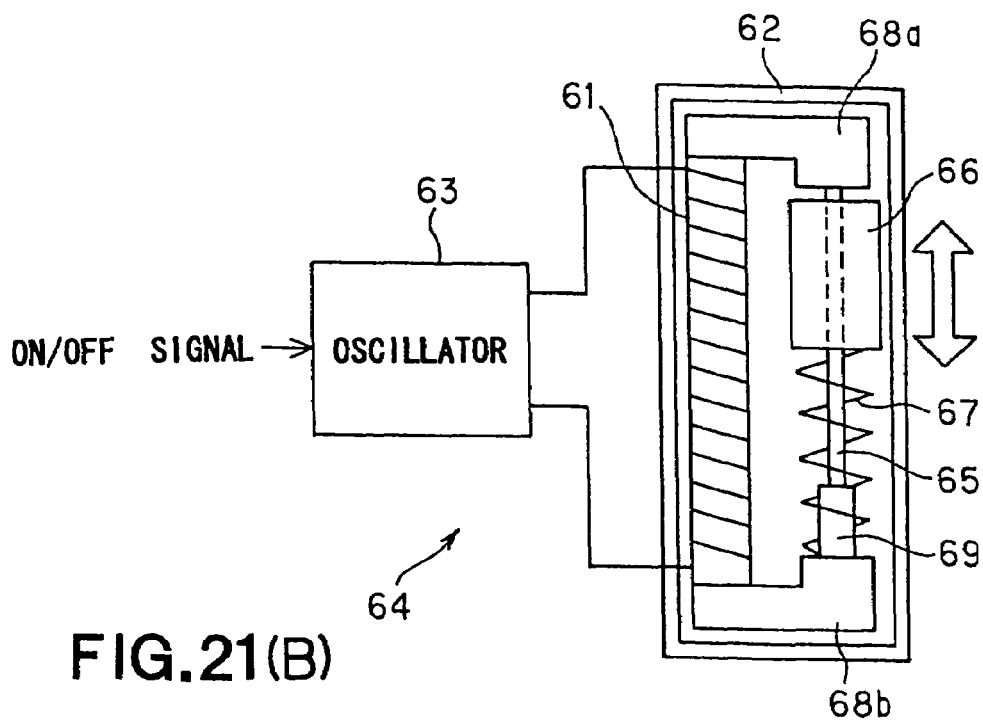
FIG. 21(A) is a view showing an arrangement of an electromagnetic solenoid device.
Figure 21B:
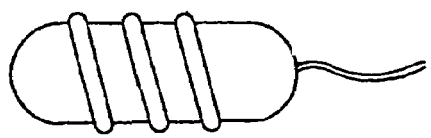
FIG. 21(B) shows a capsule type endoscope having a flexible tube at one side end.

Next, a third embodiment of the present invention will be explained with reference to FIG. 20 to FIG. 21(B). FIG. 20 shows a capsule 3C of a third embodiment of the present invention, FIG. 21(A) shows an electromagnetic solenoid device portion, and FIG. 21(B) shows an endoscope having a flexible tube disposed at one side end.

The capsule 3C shown in FIG. 20 has a built-in electromagnetic solenoid device 64. The electromagnetic solenoid device 64 electromagnetically moves a weight 66 in place of the pager motor 57 in the capsule 3B of FIG. 19(A).

As shown in FIG. 20, an electromagnetic solenoid device 64, which comprises an electromagnetic shield frame member 62 and a oscillator 63, is accommodated in an accommodating portion which is located in the vicinity of a rear end of the capsule 3C as well as adjacent to batteries 24. The electromagnetic shield frame member 62 contains an electromagnetic solenoid 61 and the like and covers them so that they are not affected by the electromagnetic from the outside. The electromagnetic solenoid 61 can be magnetized in a direction orthogonal to a center axis C of the capsule 3C, and the oscillator 63 drives the electromagnetic solenoid 61.

A vibration ON/OFF signal is sent to the capsule 3C by manipulating a vibration switch 8f of an external manipulation/input device 8 as explained in FIG. 19. On receiving the ON/OFF signal, a capsule control circuit 23 of a control substrate 53 demodulates the ON/OFF signal and sends it to the oscillator 63, thereby the oscillator 63 is oscillated. The oscillator 63 generates a current for driving the electromagnetic solenoid 61 within the range of a frequency from a direct current to several tens of hertz.

Note that the drive condition of the oscillation frequency of the oscillator 63 may be preset. Otherwise, the oscillator 63 may be arranged such that a frequency signal can be input thereto in addition to an ON/OFF signal so that it can be controlled from the outside.

When the output signal of the oscillator 63 is supplied to the electromagnetic solenoid 61 as a drive signal, the electromagnetic solenoid 61 is magnetized (generates a magnetic field).

Then, the weight 66, which is composed of, for example, a magnet movably held by a guide member 65, can be reciprocally moved in the axis direction of the guide member 65 against the elastic force of a spring 67 that urges an end of the guide member 65 (upper side in FIGS. 20 and 21(A)) according to the magnetized direction of the electromagnetic solenoid 61. The capsule 3C is vibrated in the axis direction of the guide member 65 together with the reciprocating movement of the weight 66.

FIG. 21(A) shows a more detailed structure of the electromagnetic solenoid device 64 portion in enlargement. The electromagnetic solenoid 61 and the guide member 65, which is disposed in parallel with the electromagnetic solenoid 61, are coupled with each other through presser members 68a, 68b, respectively and fixed thereby.

The weight 66, which has a hole through which the guide member 65 passes, is attached to the guide member 65 so that it is free to move in the axis direction of the guide member 65 and further urged upward by a coil-shaped spring 67 disposed under the weight 66.

Note that a stopper 69 is disposed to the presser member 68b side so that the movement of the weight 66 lower than a predetermined position is regulated by the stopper 69.

Further, in the present embodiment, the presser member 68a is composed of a non-magnetic member, and the presser member 68b is composed of a magnetic member. Note that the electromagnetic solenoid 61 is controlled by a capsule control circuit in the capsule 3C.

Further, the motion of the electromagnetic solenoid 61 can be controlled by a manipulation/input device 8 of the processing device 6 outside of a body.

A signal input from the manipulation/input device 8 likewise in FIG. 19 is transmitted to the capsule 3C through a wireless circuit 25 and transmitted to the capsule control circuit 23. The capsule control circuit 23 controls the electromagnetic solenoid 61 based on the signal.

When a drive signal of an alternate current is supplied to the electromagnetic solenoid 61, the magnetizing direction of the electromagnetic solenoid 61 is changed, thereby the weight 66 composed of the magnet is reciprocatingly moved in an up and down direction.

Accordingly, the center of gravity of the capsule 3C is displaced, thereby a force, which rotates (or inclines) the capsule 3C about the lengthwise axis thereof, is exerted.

With the above operation, a passing-through property can be improved when it is difficult to thrust the capsule 3C.

Note that the energization of the electromagnetic solenoid 61 may be repeatedly turned on and off in place of that it is driven alternately in response to the output from the oscillator 63. In this case, the weight 66 can be composed a magnetic member in place of forming it of the magnet. That is, an operation, which moves the weight 66 downward when the electromagnetic solenoid 61 is turned on and moves (returns) it upward by the elastic force of the spring 67 when it is turned off, is repeated.

That is, a force for causing the capsule 3C to swivel periodically can be generated likewise the case that the capsule 3C is driven by the output from the oscillator 63. An effect in this case is almost the same as the case of the pager motor 57.

Further, this embodiment has such a structure that the weight 66 is moved by the electromagnetic solenoid 61. However, the embodiment may be arranged such that an ultrasonic linear motor is disposed perpendicularly to the insert axis direction of the capsule type medical apparatus and the weight is attached to a drive unit of the ultrasonic linear motor.

Further, the embodiments have been described entirely as to a capsular endoscope. However, any of the embodiments is by no means limited to the capsular endoscope, and, as shown in, for example, FIG. 21(B), the same effect can be obtained even in an arrangement that a rotary sliding portion is disposed to one side end of the capsular endoscope and a catheter-like guide is provided therewith. Further, any of the vibration means described above may be disposed in the endoscope so that an extreme end of the endoscope is vibrated.

Fourth Embodiment

Figure 22:
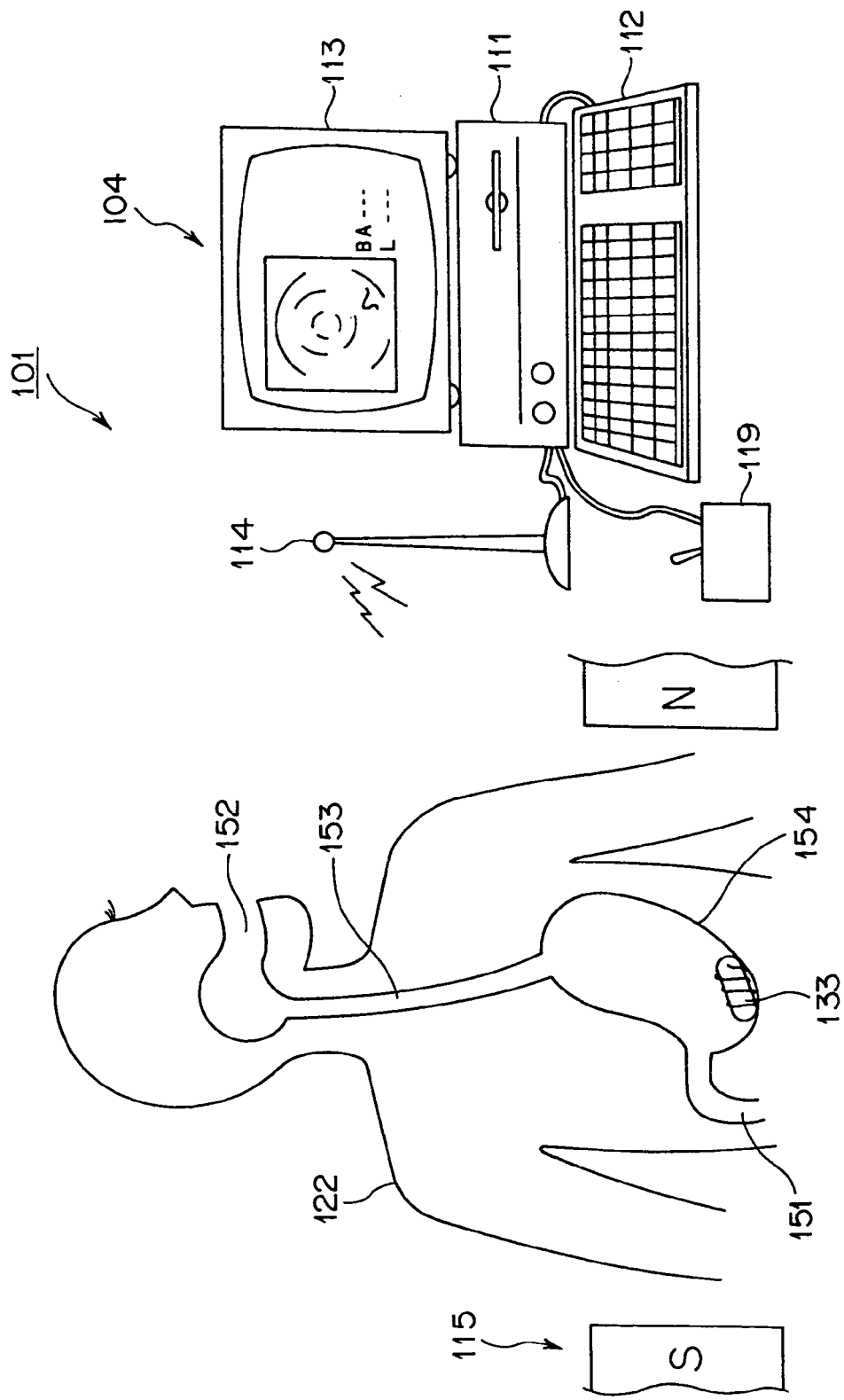
FIG. 22 is a schematic configurational view of a capsule type medical apparatus guide system having a fourth embodiment of the present invention.
Figure 23:
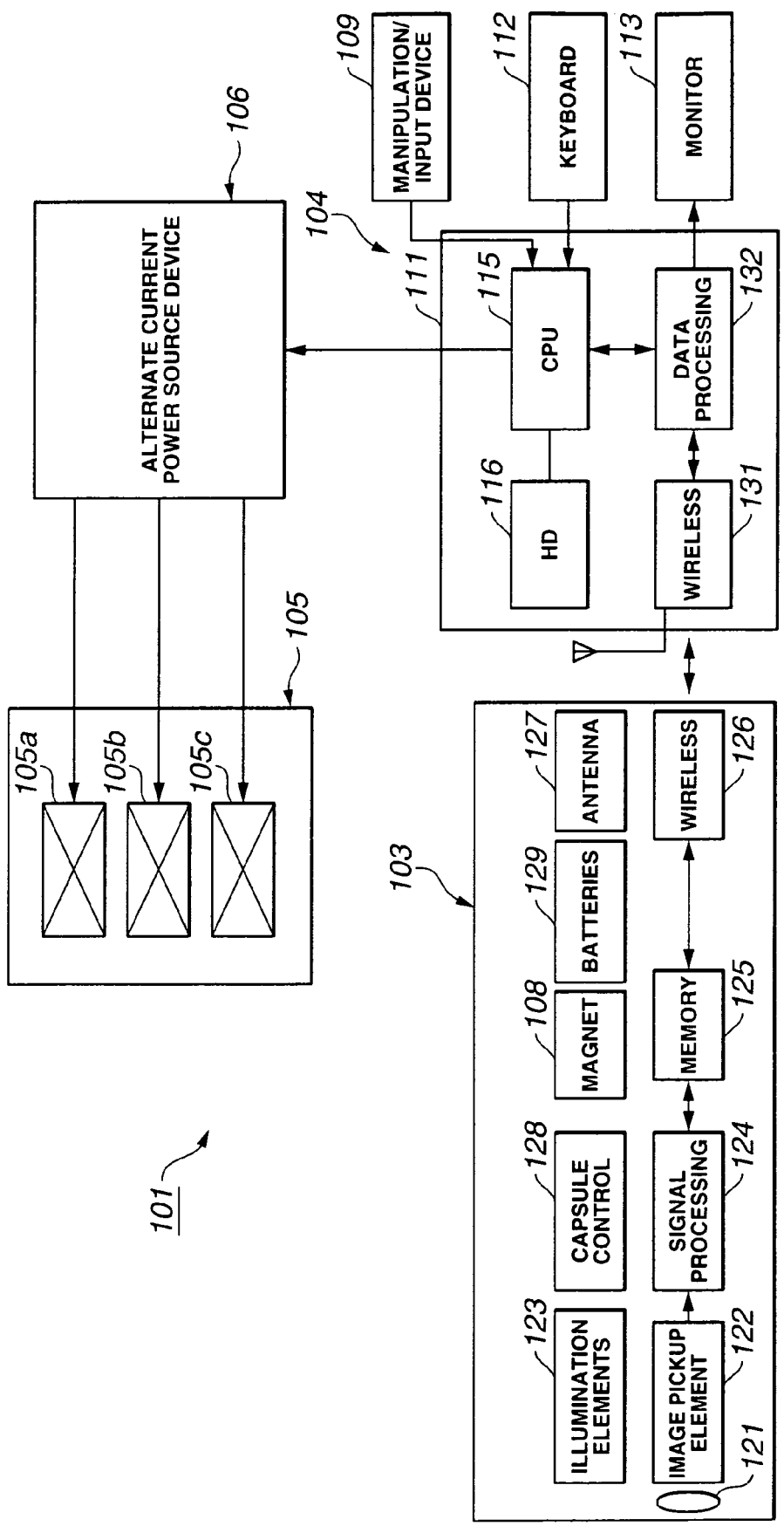
FIG. 23 is a block diagram showing a more detailed arrangement of FIG. 22.
Figure 24:
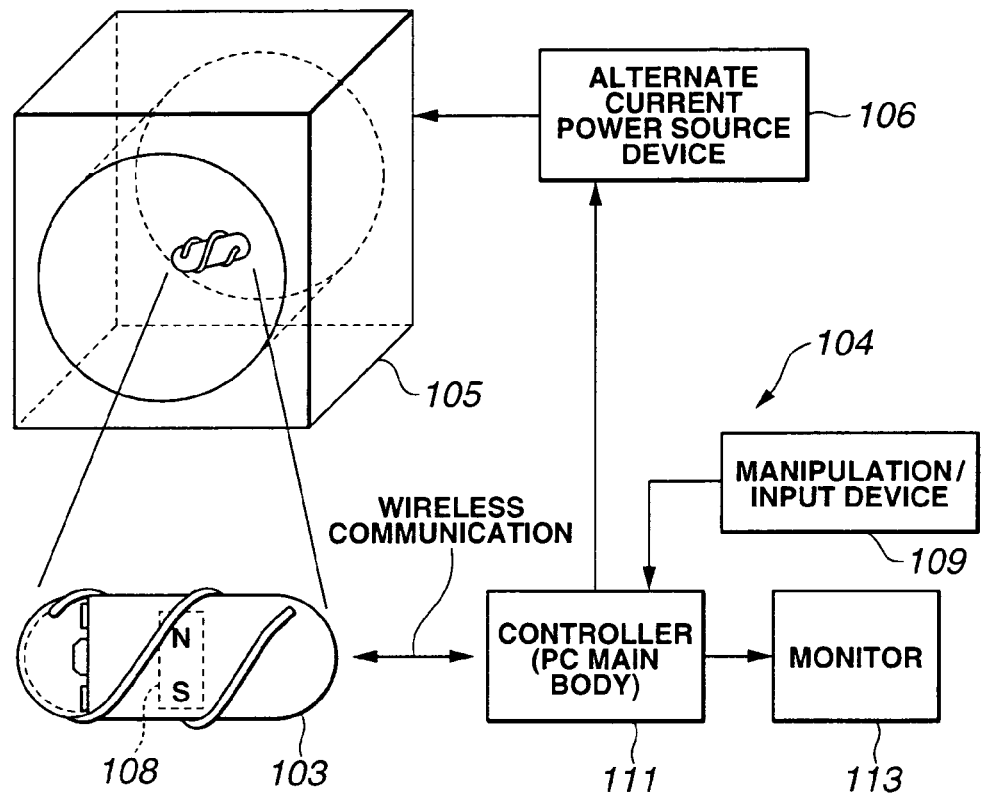
FIG. 24 is a schematic configurational view showing a schematic arrangement of a magnetic field generation device.
Figure 25:
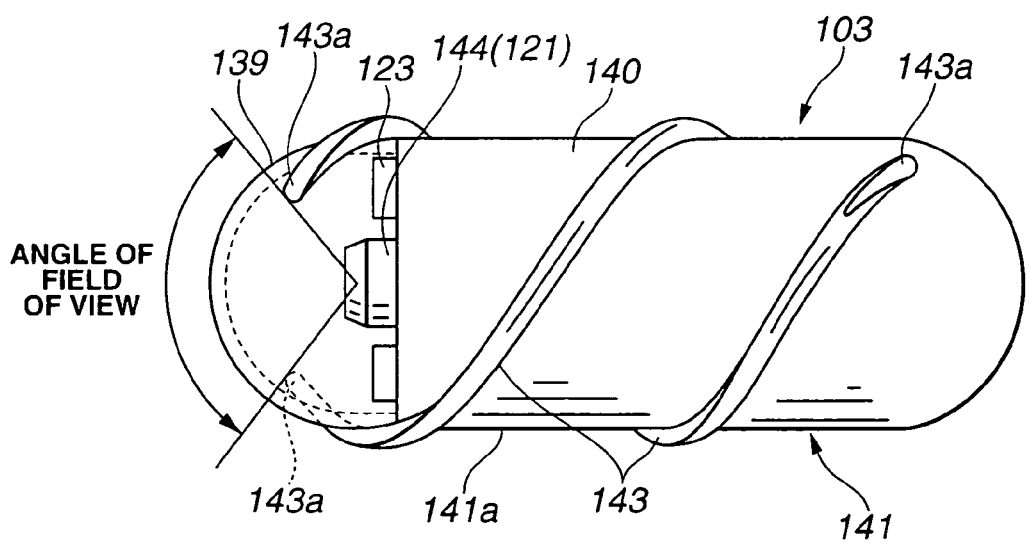
FIG. 25 is a side elevational view showing an external appearance of the capsule type medical apparatus.
Figure 26:
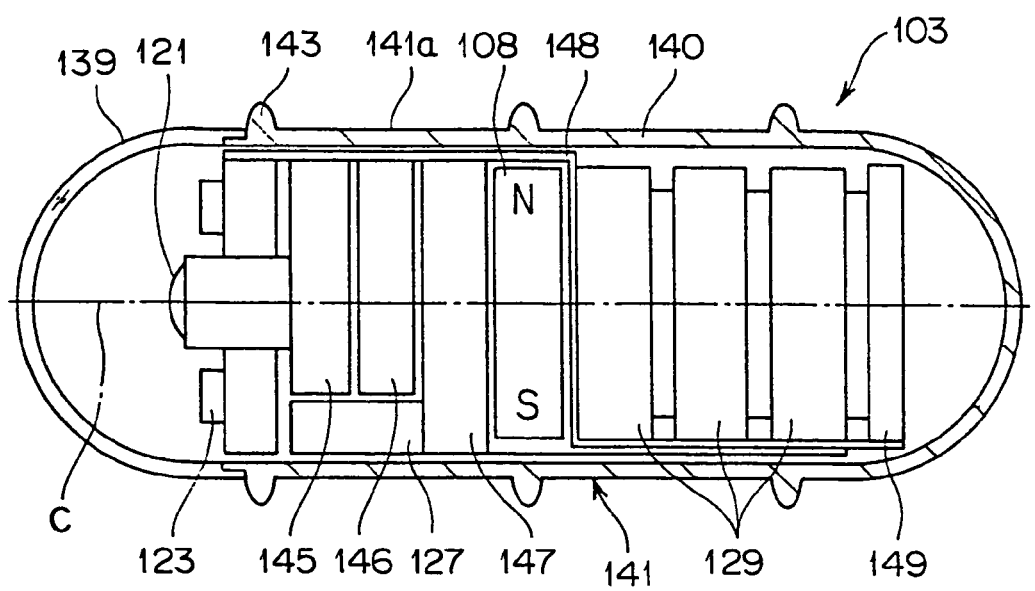
FIG. 26 is a sectional view showing an internal structure of the capsule type medical apparatus.
Figure 27:
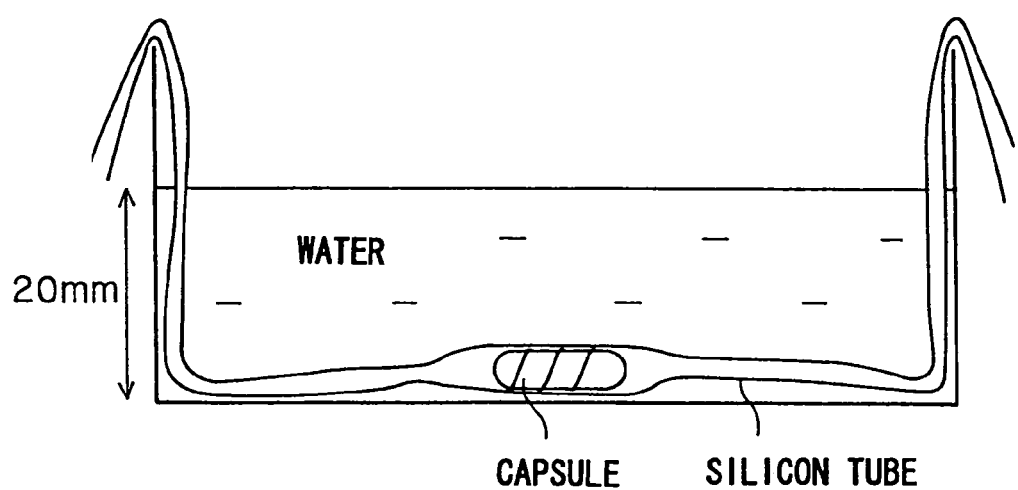
FIG. 27 is a side elevational view of a water vessel in which a sample capsule, which is inserted into a silicon tube, is dipped to measure a thrust velocity by applying a rotation magnetic field thereto.
Figure 28:
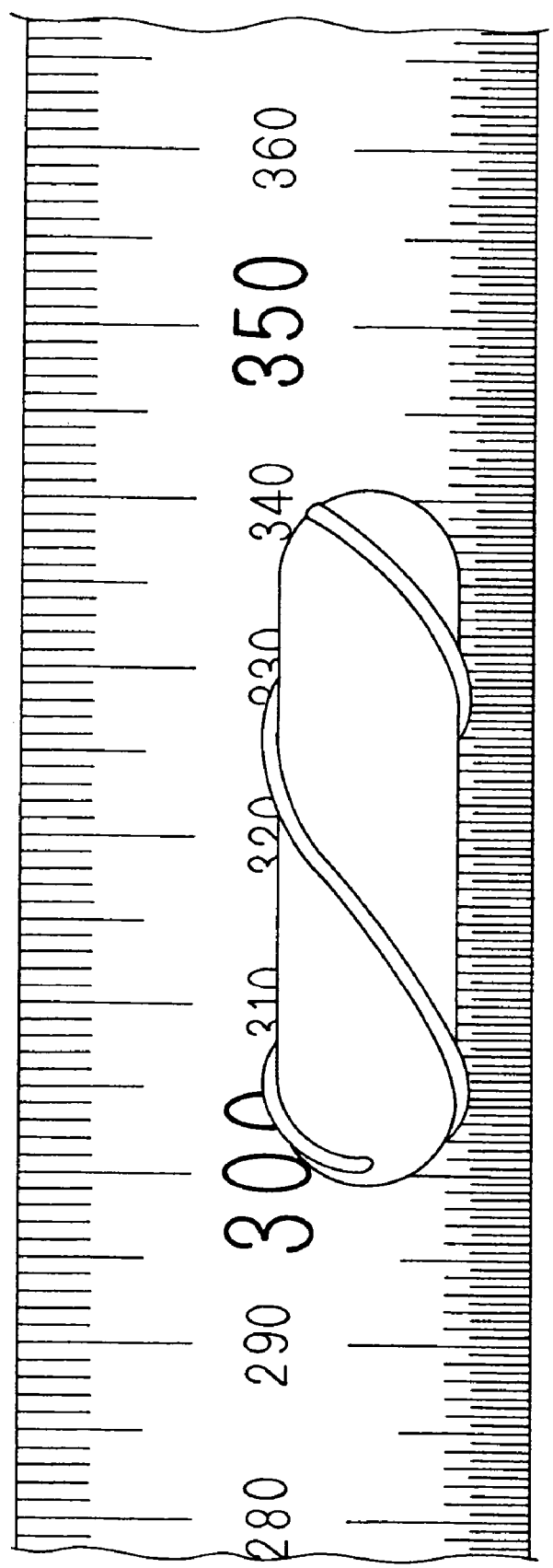
FIG. 28 is a view showing a first sample having a spiral projection disposed at an end.

FIGS. 22 to 30 relate to a fourth embodiment of the present invention, in which FIG. 22 is an overall configurational view showing an schematic arrangement of a capsule type medical apparatus guide system having a fourth embodiment of the present invention; FIG. 23 is a block diagram showing a more detailed arrangement of FIG. 21; FIG. 24 is a schematic configurational view showing a schematic arrangement of a magnetic field generation device; FIG. 25 is a side elevational view showing an external appearance of the capsule type medical apparatus; FIG. 26 is a sectional view showing an internal arrangement of FIG. 25; FIG. 27 is a side elevational view of a water vessel in which a sample capsule, which is inserted into a silicon tube, is dipped to measure a thrust velocity by applying a rotation magnetic field thereto; FIG. 28 is a view showing a sample provided with a spiral projection disposed at an end and used to measurement; FIG. 29 is a view showing a result of measurement of the thrust velocity; and FIG. 30 is an explanatory view of an action when a capsule is thrust through a curved cavity.

As shown in FIGS. 22, 23, and 24, the capsule type medical apparatus guide system (hereinafter, abbreviated as capsule guide system) 101 includes a capsule-shaped capsule type medical apparatus (hereinafter, simply abbreviated as capsule) 103, a capsule controller (hereinafter, simply abbreviated as controller) 104, a magnetic field generation device (schematically shown in FIG. 22) 105, and an alternate current power source device 106. The capsule 103 is inserted into a body cavity of a patient 102 (shown in FIG. 1) and examines the inside of the body cavity. The controller 104 is composed of a personal computer or the like which is disposed outside of the patient 102, sends and receives wireless waves to and from the capsule 103, controls the motion of the capsule 103, and receives information transmitted from the capsule 103. The magnetic field generation device 105 controls the direction and the like of a rotation magnetic field applied to the capsule 103 to thereby guide the capsule 103 in a direction where it is desired to be guided. The alternate current power source device 106 supplies an alternate electric power to the magnetic field controller 5 so that it generates a rotating magnetic field (electromagnetic field in more wide sense).

As shown in FIG. 23, the magnetic field generation device 105 is composed of, for example, three electromagnets 105a, 105b, 105c and controls the alternate current power supplied from the alternate current power source device 106 so that a rotation magnetic field is generated in three-axis directions. Note that, FIG. 24 schematically shows the magnetic field generation device 105 as a (hollow cube-shaped) three-axis Helmholtz coil formed in three-axis directions.

As shown in FIG. 23, the magnetic field generation device 105 for generating a rotation magnetic field is disposed around the patient 102, the alternate current power source device 106 is controlled from the controller 104 side, and the rotation magnetic field is applied to a magnet 108 (as a magnetic field response portion), to which a force is exerted in response to the magnetic field disposed in the capsule 103 inserted into a tract of the body cavity of the patient 102, in a direction where the capsule 103 is thrust. With this operation, the capsule 103 can be smoothly and effectively thrust (guided).

The direction of the rotation magnetic field, which is generated by the magnetic field generation device 105, can be controlled by manipulating a manipulation/input device 8 connected to the magnetic field generation device 104.

As shown in FIG. 23, the controller 104 includes a personal computer main body 111, a keyboard 112, a monitor 113 as display means, an out-of-body antenna 114, and a manipulation/input device 109. The personal computer main body 111 has a function for controlling the capsule 103 and (the alternate current source 106) of the magnetic field generation device 105; the keyboard 112 is connected to the personal computer main body 111, and commands, data, and the like are input therethrough; the monitor 113 is connected to the personal computer main body 111 and displays an image and the like, the out-of-body antenna 114 is connected to the personal computer main body 111, oscillates a control signal for controlling the capsule 103, and receives the signal from the capsule 103; and the manipulation/input device 109 is connected to the personal computer main body 111, and the direction of the rotation magnetic field, and the like are input therethrough.

As shown in FIG. 23, the controller 104 has a built-in CPU 115 which creates control signals for controlling the capsule 103 and the magnetic field generation device 105 based on inputs from the keyboard 112 and the manipulation/input device 109 or on a control program stored in a hard disc 116 (refer to FIG. 23) in the personal computer main body 111.

The control signal for controlling the magnetic field generation device 105 is transmitted from the personal computer main body 111 to the alternate current power source device 106 through a connection cable. The rotation magnetic field is generated based on the control signal. The rotation magnetic field generated by the magnetic field generation device 105 is magnetically exerted on the magnet 108 in the capsule 103 and the capsule 103 is rotated thereby. As a result, a power for thrusting the capsule 103 is obtained from a thrust generation structural portion described later.

In contrast, the control signal for controlling the capsule 103 is modulated by a carrier wave having a predetermined frequency through an oscillation circuit in the personal computer main body 111 and oscillated from the out-of-body antenna 114 as a wireless wave.

Then, the capsule 103 receives the wireless wave as the control signal through an antenna 127 to be described later and outputs the control signal to respective constitution circuits and the like after it is demodulated.

Further, the controller 104 receives information (data) signals such as a video signal and the like transmitted from the wireless antenna 127 of the capsule 103 through the out-of-body antenna 114 and displays them on the monitor 113.

As shown in FIG. 23, accommodated in the capsule 103 are a signal processing circuit 124, a memory 125, a wireless circuit 126, the antenna 127, a capsule control circuit 128, and a battery 129, in addition to an objective optical system 121 for imaging an optical image, an image pickup element 122 disposed at the image pickup position of the objective optical system 121, illumination elements 123 disposed around the objective optical system 121, and the magnet 108. The signal processing circuit 124 subjects the signal picked up by the image pickup element 122 to signal processing; the memory 125 temporarily stores the digital video signal created by the signal processing circuit 124; the wireless circuit 126 modulates the video signal read from the memory 125 with a high frequency signal and converts it into a signal to be wireless transmitted, modulates the control signal transmitted from the controller 104, and so on; the antenna 127 transmits and receives wireless waves to and from the out-of-body antenna 114; the capsule control circuit 128 controls the capsule 103 such as the signal processing circuit 124 and the like, and the battery 129 supplies an operation power to an electric system in the capsule 103 such as the signal processing circuit 124 and the like.

Further, the personal computer main body 111, which constitutes the controller 104 for executing a wireless communication with the capsule 103, includes a wireless circuit 131, a data processing circuit 132, the CPU 115 as control means, and the hard disc 116. The wireless circuit 131 is connected to the out-of-body antenna 114 and executes a wireless communication with the wireless circuit 126 (on the capsule 103 side); the data processing circuit 132 is connected to the wireless circuit 131 and subjects the image data sent from the capsule 103 to data processing such as image display processing and the like; the CPU 115 controls the data processing circuit 132, the alternate current power source device 106, and the like; and the hard disc 116 stores programs, data and the like. The CPU 115 is connected to the manipulation/input device 109 for setting the direction of the rotation magnetic field and to the keyboard 112 through which commands and data are input.

The monitor 113 is connected to the data processing circuit 132, and the image, which is recorded by the image pickup element 122 and processed by the data processing circuit 132 through the wireless circuits 126 and 131, and the like are displayed thereon. Further, since images are recorded while the capsule 103 is being rotated, the data processing circuit 132 executes processing for correcting the directions of the images to be displayed on the monitor 113 to a predetermined direction so that an operator can observe the images easily.

FIG. 25 shows an outer shape of the capsule 103, and FIG. 26 shows an inside structure thereof.

As shown in FIGS. 25 and 26, the capsule 103 is airtightly covered with, for example, a hemispherical transparent extreme end cover 139 and a cylindrical main body exterior member 140 to which the extreme end cover 139 is connected airtightly. With this arrangement, an approximately cylindrical capsule main body 141 whose inside is hermetically sealed is formed. Note that the rear end of the main body exterior member 140 is formed in an approximately hemispherical shape. As shown in FIG. 26, the outside shape of the capsule main body 141 is formed symmetrically in rotation about the lengthwise center axis C of the capsule main body 141 which is also a traveling direction of the capsule main body 141.

Further, a thrust generating spiral structure, which converts a rotational motion into a thrust, is disposed on the outside surface of the rotation-symmetrical capsule main body 141. The spiral structure has spiral projections 143 which spirally project from the cylindrical outer circumferential surface (base surface) 141a of the capsule main body 141 and come into contact with the inside wall of body cavity to thereby convert the rotational motion into the thrust. Further, a spiral groove is formed between the adjacent spiral projections 143 so that gases and fluids such as body fluids and the like in body cavity can communicate with each other back and forth through the groove.

The components such as the objective lens 121, the illumination elements 123 and the like described above are accommodated and disposed in the capsule main body 141.

More specifically, the objective lens 121 is disposed at central portion of the capsule main body 141 inwardly of the extreme end cover 139 thereof in the state that it is attached to a cylindrical lens frame 144, an image pickup element substrate 145, on which the image pickup element 122 is mounted, is disposed at an image pickup position of the objective lens 121, and the plurality of illumination elements 123 are disposed around the lens frame 144.

A control substrate 146, which executes signal processing and control, and a communication substrate 147, which has functions of the wireless circuit 126 and the like, are disposed adjacent to the image pickup element substrate 145 as if they are laminated, and the antenna 127 is connected to the communication substrate 147. Further the illumination elements 123, the image pickup element substrate 145, and the like are electrically connected through a flexible substrate 148.

Further, the magnet 108 is disposed approximately at central position of the length on the lengthwise center axis C of the capsule 103 such that the direction of the magnet 108 orthogonal to the center axis C becomes the lengthwise direction thereof and fixed by a not shown adhesive or the like.

Further, the battery 129 is accommodated adjacent to the magnet 108 and connected to a flexible substrate 148 through a switch circuit 149.

Since the magnet 108 is disposed at the central position on the center axis C of the capsule main body 141 with the magnetizing direction thereof in a direction perpendicular to the center axis C, the rotation magnetic field generated by the magnetic field generation device 105 is exerted on the magnet 108, and the capsule 103 is rotated by the rotation force received by the magnet 108.

It should be noted that the magnet 108 used here is a permanent magnet such as a neodymium magnet, samarium cobalt magnet, ferrite magnet, chromium cobalt magnet, platinum magnet, AlNiCo magnet, and the like.

Since the rare earth magnets such as the neodymium magnet and the samarium cobalt magnet have a strong magnetic force, they have a merit in that the size of the magnet built in the capsule can be reduced. In contrast, the ferrite magnet has a merit in that it is less expensive. Further, the platinum magnet is excellent in corrosion resistance.

Further, in the present embodiment, as shown in FIG. 25, the extreme end sides of the spiral projections 143, which are formed on the outside surface of the capsule main body 141, extend up to a side of the capsule 103 where it is formed in a hemispherical shape with its diameter reduced passing through the cylindrical outer circumferential surface of the capsule 103, and the end portions 143a of the spiral projections 143 are formed in a midstream of the diameter-reduced hemispherical portion of the capsule 103, more specifically, at positions which are not covered by the field angle of the objective lens 121. Further, the rear ends 43b of the spiral projections 143 extend to the vicinity of the boundary of the capsule 103 where it is formed in the hemispherical shape with its diameter reduced. Note that, in the example shown in FIG. 25, the spiral projections 143 are formed double (two lines) with one of the spiral projections 143 being disposed at an intermediate position of the other spiral projection 143.

In the embodiment arranged as described above, the spiral projections 143 are disposed around the outer circumferential surface of the capsule 103 as well as one end portions 143a thereof are formed up to the positions which reach the vicinity of the end of the diameter-reduced portion. That is, the spiral projections 143 have a feature in that although they are formed around the cylindrical outer circumferential surface portion of the capsule main body 141, the one end portions 143a further extend up to, for example, the spherical portion whose diameter is made smaller than that of the cylinder and reach the boundary position which is not covered by the field angle (imaging area).

Since the spiral projections 143 are disposed up to the vicinity of the end of the capsule main body 141, a thrust function is enhanced as explained below.

FIG. 27 shows a water vessel for measuring a thrust velocity using the capsule main body 141 having the spiral projections 143 formed to the vicinity of the end of thereof. A sample (first sample) having (the outside shape structure of the capsule 103 of the present embodiment) is dipped in the water vessel in the state that it is inserted into a silicon tube that simulates a cavity organ, water is poured into the water vessel from an upper side (water depth is, for example, 20 cm) so that a water pressure is exerted on the tube, and the thrust velocity of the sample is measured by moving it, for example, 2 cm by applying a rotation magnetic field thereto from the outside.

Further, the thrust velocity of a comparative sample (second sample), which has the spiral projections of the first sample formed around only a cylindrical surface portion, is measured under the same condition. FIG. 28 shows the outside shape of the first sample. Note that the second sample has the spiral projections formed only on the cylindrical surface thereof in the first sample shown in FIG. 28.

FIGS. 29(A) and 29(B) show results of measurement obtained using these samples. The results of measurement shown in FIGS. 29(A) and 29(B) are obtained by plotting the average values of measurements executed 10 times. The frequency of the rotation magnetic field is set to 0.5 Hz, 1 Hz, and 5 Hz.

Further, it is assumed that the thrust velocity is proportional to the frequency, and lines, which are linearly approximated by a least squares method, are drawn.

FIGS. 29(A) and 29(B) show the results of the same experiment by changing a scale of a frequency and a velocity. Note that the data shown by circles is obtained by the sample having no spiral projections formed at the extreme end (simply abbreviated as without extreme end in FIG. 29(A)), and the data shown by triangles is obtained by the sample having the spiral projections formed also at the extreme end. Further, FIG. 29(A) shows the case of a frequency and a velocity up to 5 Hz, and FIG. 29(B) shows the result of measurement up to 1 Hz in enlargement.

It can be said from the data of measurement that the thrust velocity of the sample, which has the spiral projections formed up to the end portion, is about 1.4 times larger than that of the sample without the spiral projections in the vicinity of the end portion. It can be said that this exhibits that the spiral projections at the end portion contribute to the thrust force.

Further, another characteristic action achieved by the capsule 103 of the present embodiment will be explained with reference to FIGS. 30(A) and 30(B).

Figure 30A:
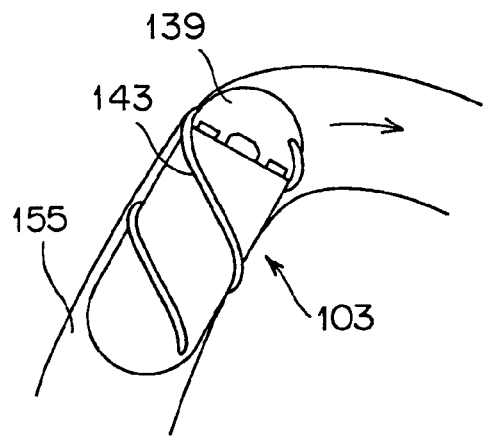
FIGS. 30(A) and 30(B) are explanatory views showing an action when the capsule thrusts in a curved tract.
Figure 30B:
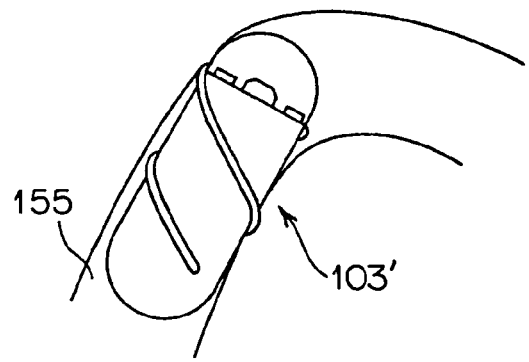

When it is intended to thrust a capsule in a curved direction of, for example, a curved cavity organ 155 as shown in FIGS. 30(A) and 30(B), it is difficult to thrust a capsule 103' having the spiral projections formed only around a cylindrical portion as shown in FIG. 30(B) even if it is rotated. This is because that the spiral projections are unlike to be engaged with the concavo-convex portions such as folds on the inside wall of the cavity organ, and thus it is difficult to smoothly thrust the capsule 103'.

In the present embodiment, however, since the spiral projections 143 are formed up to the vicinity of the end portion whose diameter is further reduced as shown in FIG. 30(A), the capsule 103 can be more smoothly rotationally thrust even in the above state by engaging the spiral projections 143, which are formed up to the vicinity of the diameter-reduced portion, with the concavo-convex portions of the inside wall of the cavity organ.

As described above, this embodiment is characterized in that the thrust force can be enhanced and the capsule 103 can reach a target portion in a short time because the capsule 103 is rotationally driven by disposing the spiral structure, more specifically, the spiral projections 143 also in the vicinity of the diameter-reduced end portion as well as the capsule 103 can be more smoothly thrust along a curved tract by the spiral projections 143 formed also in the vicinity of the end portion.

Next, an operation of the capsule guide system 101 provided with the spiral projections 143 will be explained below.

As shown in FIG. 22, when it is necessary to observe the inside of the body cavity of, for example, a duodena 151 side, an intestinum tenue side, or the like of the patient 102, the operator causes the patient 102 to swallow the capsule 103 from a mouth 152.

Note that, at this time, the operator previously turns on the switch circuit 149 of the capsule 103 just before the patient 102 swallows it so that the power of the battery 129 is supplied to the illumination elements 123 and the like. Simultaneously with the above operation, the operator starts (turns on) the magnetic field generation device 105 and magnetically controls the capsule 103 so that it is caused to easily reach a target portion side in the body cavity by the rotation magnetic field generated by the magnetic field generation device 105.

As described above, in the capsule 103, when the magnet 108 acts on the rotation magnetic field generated by the magnetic field generation device 105, the capsule main body 141 is rotated by the action received by the magnet 108. When the capsule main body 141 comes into contact with the inside wall of the body cavity, a friction force between the membrana mucosa of the inside wall of the body cavity and the spiral projections 143 is converted into a large thrust force, thereby the capsule 103 is moved forward and backward. Further, the traveling direction (direction) of the capsule 103 is changed while the capsule main body 141 is being rotated so that the rotation plane of the magnet 108 agrees with the rotation plane of the rotation magnetic field as the rotation magnetic field rotates.

At this time, in the capsule 103, capsule main body 141 can thrust toward the target portion side in the tract of the body cavity.

Since the capsule 103 is swallowed by the patient 102, it passes through the esophagus 153 from the oral cavity 152 and reaches the inside of a stomach 154.

When it is necessary to observe the inside of the stomach 154, the operator depresses a key corresponding to an observation start command from, for example, the keyboard 112 of the controller 104. Thus, a control signal input from the key is radiated as a wireless wave through the out-of-body antenna 114 of the controller 104 and transmitted to the capsule 103 side.

The capsule 103 detects a motion start signal from the signal received through the antenna 127, thereby the illumination elements 123, the image pickup element 122, the signal processing circuit 124, and the like are placed in a drive state.

The illumination elements 123 emit illumination light in the direction of the field of view of the objective lens 121, and an optical image in the range of the illuminated field of view is formed on the image pickup element 122 located at the image pickup position of the objective lens 121 and photoelectrically converted. A resultant optical image is subjected to A/D conversion by the signal processing circuit 124 and converted into a digital signal, which is stored in the memory 125 after it is subjected to compression processing. Thereafter, the compressed digital signal is modulated by the wireless circuit 126 and radiated from the antenna 127 as a wireless wave.

The wireless wave is received by the out-of-body antenna 114 of the controller 104, demodulated by the wireless circuit 131 in the personal computer main body 111, further converted into a digital video signal by the data processing circuit 132 through A/D conversion, and stored in the memory of the data processing circuit 132 or in the hard disc 116. Then, the digital video signal is read out at a predetermined velocity, and the optical image recorded by the image pickup element 122 is displayed on the monitor 113 in color.

The operator can observe the inside of the stomach 154 of the patient 102 through the observation of the image. The operator can easily control an external magnetic force to be exerted using the manipulation means such as the joy stick and the like of the manipulation/input device 109 while observing the image so that the operator can observe the entire region of the stomach 154.

Further, on the completion of observation of the inside of the stomach 154, the operator can magnetically guide and move the capsule 103 from the stomach 154 to the duodena 151 side by controlling the direction of the rotation magnetic field generated by the magnetic field generation device 105 with respect to the capsule 103. Then, the operation can smoothly thrust the capsule 103 also in the duodena 151 by controlling the direction of the rotation magnetic field so that the capsule 103 travels in the direction of the body cavity of the duodena 151.

Further, when the capsule 103 is caused to travel in a curved tract such as the intestinum tenue, it can be caused to smoothly travel even in the curved tract. This is because that the spiral projections 143 are formed up to the vicinity of the spherical end portion of the capsule main body 141 as explained in FIG. 30(A).

As described above, according to this embodiment, since the capsule 103 can be smoothly thrust, an examination time can be shortened as well as a burden, fatigue and the like of the operator and the patient can be reduced.

Further, since the capsule 103 of the present embodiment does not move uselessly, a magnetic field guide efficiency can be enhanced, which is also effective in that the magnet 108 in the capsule main body 141 and the electromagnets 105a, 105b, 105c disposed outside of the body can be reduced in size.

Fifth Embodiment

Figure 31:
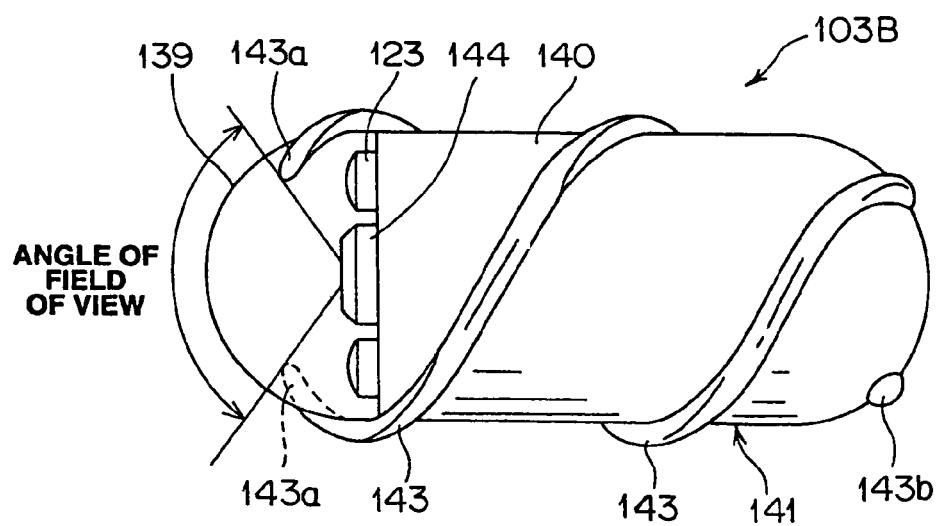
FIG. 31 is a side elevational view showing a capsule type medical apparatus of a fifth embodiment of the present invention.

Next, a fifth embodiment of the present invention will be explained with reference to FIG. 31. FIG. 31 shows a capsule 103B of the fifth embodiment of the present invention. In the capsule 103B, spiral projections extends further backward and formed up to the vicinity of the end portion of a capsule main body 141, in contrast to the capsule 103 of the fourth embodiment in which the rear ends 143b of the spiral projections 143 are located at positions in front of the rear end of the capsule main body 141.

The other arrangement of the capsule 103B is the same as that of the capsule 103 of the fourth embodiment.

As an operation and advantage of the present embodiment, even when the capsule 103B is moved backward, it can be moved effectively as well as when capsule 103B is moved to a curved rear side, it can be also moved smoothly.

Figure 32:
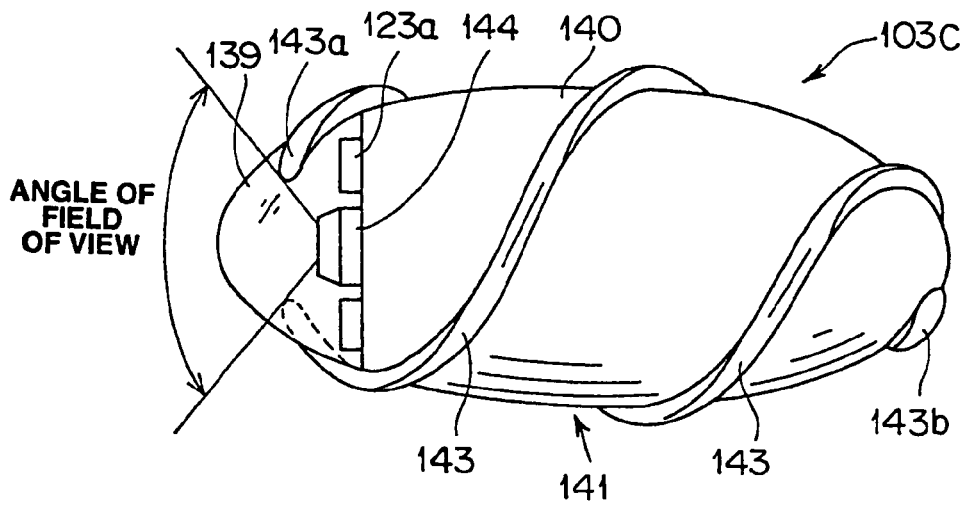
FIG. 32 is a side elevational view showing a capsule type medical apparatus of a first modification.

FIG. 32 shows a capsule 103C of a first modification. The outside diameter of the capsule 103C smoothly changes from an extreme end to a rear end like a leaf roll shape, in contrast that the outside shape of the capsule 103B shown in FIG. 31 is formed in a hemispherical shape.

Since the outside diameter of the capsule 103C smoothly changes from the extreme end to the rear end, it has an excellent insert property.

Figure 33:
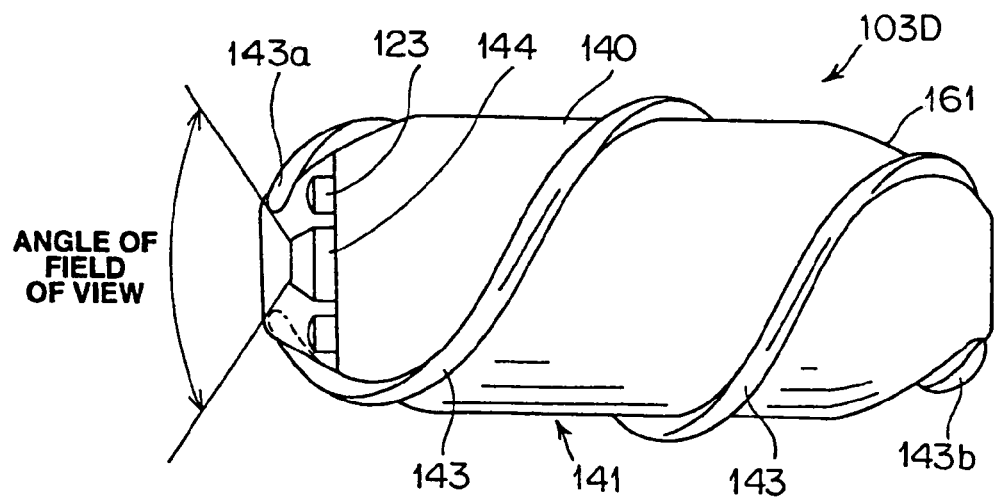
FIG. 33 is a side elevational view showing a capsule type medical apparatus of a second modification.

FIG. 33 shows a capsule 103D of a second modification. In the capsule 103D shown in FIG. 33, the outside shape of the capsule main body 141 thereof is formed to have taper portions 161 with their diameters reduced by forming both the ends of a central cylindrical portion of the capsule main body 141 in a taper shape (conical shape). Then, the extreme end and rear end sides of the capsule main body 141 are formed in a flat shape as if they are cut away.

A good insert property can be obtained because the extreme end cover side and the rear end side are formed in the diameter-reduced taper shape. Further, since the extreme end cover side and the rear end side are formed in the cut-away shape, the capsule 103D can be reduced in size.

Figure 34:
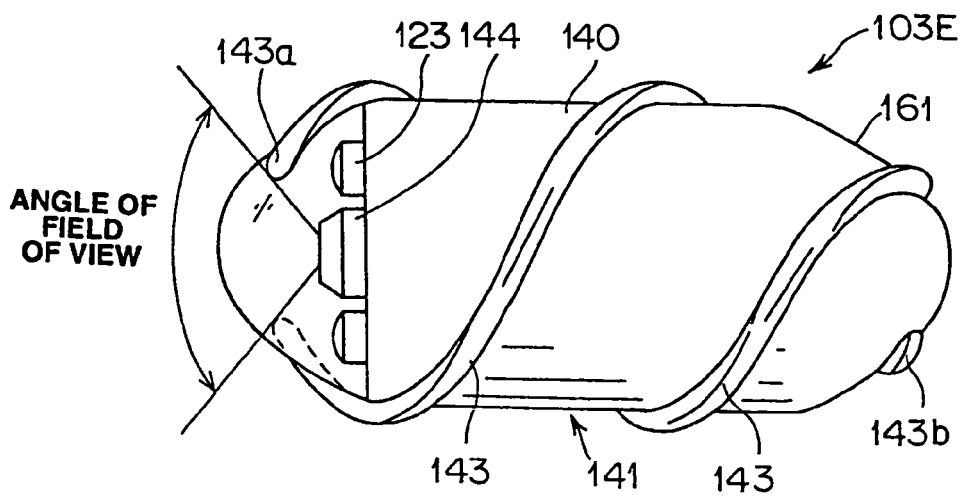
FIG. 34 is a side elevational view showing a capsule type medical apparatus of a third modification.

FIG. 34 shows a capsule 103E of a third modification. The capsule 103E shown in FIG. 34 is arranged by rounding the extreme end and the rear end of the capsule 103D of FIG. 33 in an approximately spherical shape in place of the flat shape.

That is, in the capsule 103E, the outside shape of a capsule main body 141 is formed to have taper portions 161 with their diameters reduced by forming both the ends of a central cylindrical portion of the capsule main body 141 in a taper shape (conical shape). Then, the extreme end side and rear end side ends of the capsule 103E are formed in an approximately spherical shape.

A good insert property can be obtained in the modification because the extreme end cover side and the rear end side are formed in the diameter-reduced taper shape.

Figure 35:
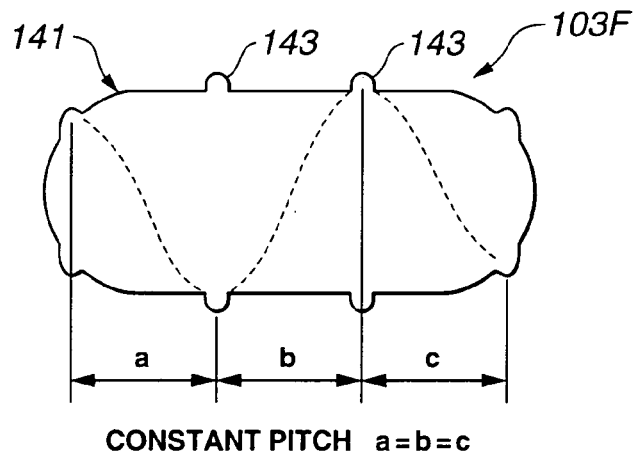
FIG. 35 is a schematic side elevational view showing a pitch of a spiral projection of a capsule type medical apparatus of a fourth modification.

FIG. 35 shows a capsule 103F of a fourth modification. In the capsule 103F shown in FIG. 35, a pitch b, at which spiral projections 143 are formed in a spiral shape on the outside surface of a capsule main body 141 in, for example, central portion thereof having a largest outside diameter, is set same as pitches a and c, at which the spiral projections 143 are formed in the portions of the capsule main body 141, which are located on the extreme end side and the rear end side of the central portion and have a smaller outside diameter, that is a=b=c.

Since the spiral projections 143 are formed on the outside surface of the capsule 103F at the constant pitch, when the capsule 103F rotates and is pushed out by being engaged with the concavo-convex portions of the inside wall surface of cavity organ, the capsule 103F can be effectively thrust because it is contemplated that the concavo-convex portions of the inside wall surface of the cavity organ remain approximately invariant.

Further, the pitches are set constant, when the capsule main body 141 is made by machining, it can be simply machined by setting an amount of feed of a lathe constant with respect to the rpm thereof, thereby the capsule main body 141 can be made at low cost. Further, since the amount of feed per rotation of the capsule 103F in a small diameter portion is the same as that in a large diameter portion, a thrust can be effectively generated in the capsule 103F in its entirety.

Further, a fifth modification may be arranged as described below.

The respective capsules 103B and the like described above are arranged as a type without cable having neither a line nor a tube attached to a rear portion. However, they may be arranged as capsule type medical apparatuses of a type with a cable which have a flexible tube freely rotatably attached to the rear portion thereof (on the side opposite to the extreme end cover 139).

In this case, the capsule type medical apparatuses can be more effectively thrust or moved backward by combining the thrust executed by the spiral structure with the pulling and pushing executed by the tube.

Sixth Embodiment

Next, a sixth embodiment of the present invention will be explained with reference to FIGS. 36(A) and 36(B). FIG. 36(A) shows a capsule 103G of the embodiment, and FIG. 36(B) shows an example of an image obtained by the capsule 103G.

The capsule 103G shown in FIG. 36(A) is arranged such that a hollow structure is provided with the spiral projections 143 of, for example, the capsule 103 of FIG. 31 by forming hollow portions 162 in the spiral projections 143 along the lengthwise direction thereof, the hollow portions 162 having open ends 162a which open in the end portions 143a on the extreme end side of the spiral projections 143. In addition to the above, the end portions 143a are extended to positions which are located inwardly of a view angle so that the end portions 143a can be observed (on an obtained image) as shown in FIG. 36(B).

Further, in the capsule 103G, a hollow portion is formed in a capsule main body 141, an accommodating portion 164, in which a medicine can be stored, is formed in the hollow portion, and a micro pump 166, which drives for feeding (or discharging) and suctioning, is interposed between the accommodating portion 164 and a tube 165 which connects the accommodating portion 164 to the hollow portions 162 of the spiral projections 143. With this arrangement, the medicine 163 stored in the accommodating portion 164 is discharged to the open ends 162a at the extreme end through the hollow portions 162 of the spiral projections 143 so that the patient and the like can be subjected to a therapeutic treatment by the medicine given to an affected area and the like.

Further, when the micro pump 166 is rotated inversely, it can suction inside-body substances such as a body fluid and the like from the open ends 162a and accommodate them in the accommodating portion 164. For example, first, the medicine 163 stored in the accommodating portion 164 is discharged to the affected area and the like from the open ends 162a. Thereafter, the inside-body substances such as the body fluid and the like are accommodated in the accommodating portion 164 by rotating the micro pump 166 inversely, and the capsule 103G is discharged from the inside of the body. Then, the inside-body substances are taken out from the capsule 103G and can be examined in detail.

According to this embodiment, since the spiral projections 143 as the spiral structure are also used to discharge the medicine 163, the spiral structure can be used to thrust the capsule 103G and to discharge the medicine 163, thereby the capsule 103G, which is small in size and has a function for picking up an image of the inside of a body cavity and a function for discharging the medicine for the treatment, can be realized.

Further, there can be realized the capsule 103G having a function for collecting inside-body-cavity substances such as a body fluid in a body cavity and the like.

Further, since the end portions 143a of the spiral projections 143 are extended to the positions inwardly of the view angle, a thrust can be more enhanced as well as the medicine 163 can be discharged from the open ends 162a disposed to the end portions 143a, and when the inside-body substances are suctioned, a suctioning operation can be confirmed on an obtained image.

Figure 36:
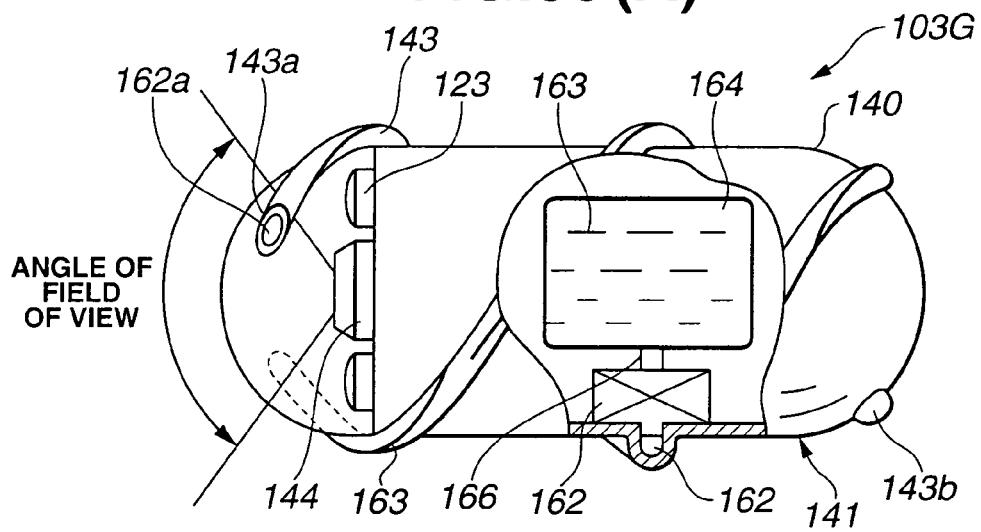
FIG. 36(A) is an explanatory view showing a capsule type medical apparatus of a sixth embodiment of the present invention.
FIG. 36(B) is a view showing an image obtained from the capsule type medical apparatus shown in FIG. 36(A)
Figure 36:
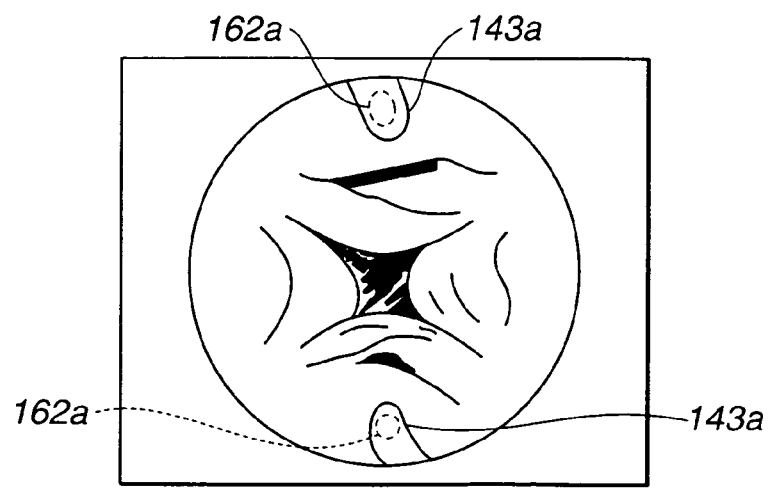

Note that the capsule 103G of FIG. 36 may be used only to discharge the medicine 163 and only to suction and collect the inside-body substances.

Various sensors such as pressure sensor, pH sensor, temperature sensor, blood sensor, and the like may be disposed at the open ends 162a of the hollow portions of the spiral projections 143, and the wirings of the sensors may be disposed along the hollow portions 162. A different type of sensors may be disposed to each of the plurality of spiral projections 143 or the same type of sensors may be disposed to it. This arrangement is more convenient because the portions and positions measured by the sensors can be confirmed on an image simultaneously with the discharge of the medicine 163 or the collection of the body fluid.

Figure 37:
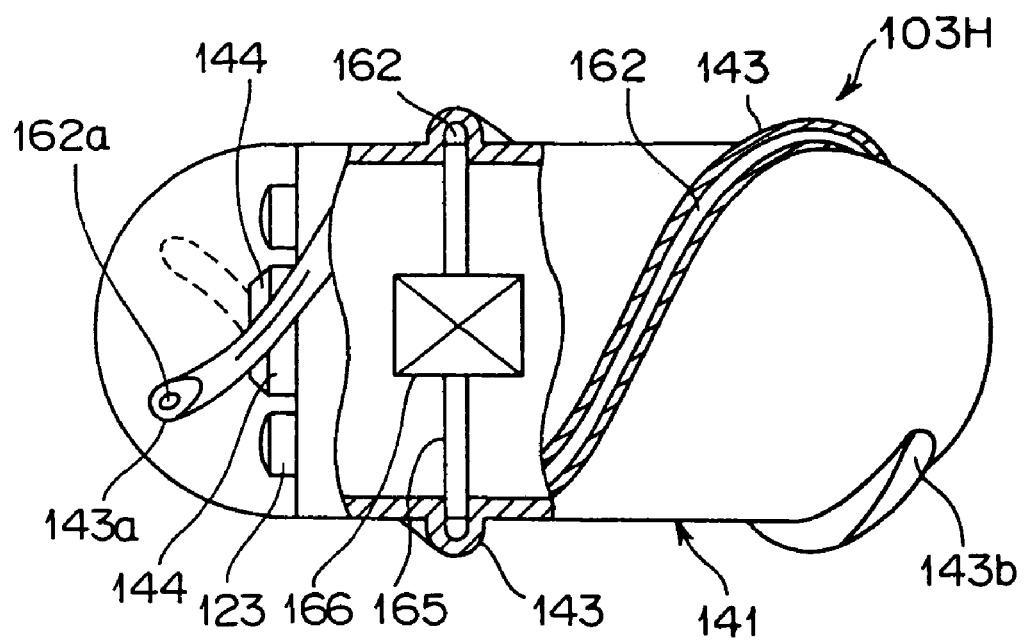
FIG. 37 is a side elevational view, partly in cross section, showing an arrangement of a capsule type medical apparatus of a modification.

FIG. 37 shows a capsule 103H of a modification. The capsule 103H is arranged such that the accommodating portion 164 is not disposed in the capsule 103 of FIG. 36(A), and a micro pump 166 disposed in the capsule 103H is connected to the hollow portions 162 of two spiral projections 143 formed double.

When the micro pump 166 is rotated, for example, clockwise, it executes a suctioning operation from an upper side to a lower side in FIG. 37, thereby the body fluid and the like can be suctioned into the hollow portion 162 of a spiral projection 143 whose cross section is shown in FIG. 37 and stored therein.

Further, when the micro pump 166 is rotated counterclockwise, the body fluid and the like can be suctioned into the hollow portion 162 of the other spiral projection 143 and stored therein.

That is, in this modification, it is possible to suction the inside-body substances such as the body fluid and the like and substances to be examined from, for example, different portions into the hollow portions 162 of the spiral projections 143 disposed double and collect them therein. This modification has substantially the same advantage as that of the capsule 103H of FIG. 36.

Note that the magnetic field response portion, which is built in the capsule 103 and the like and acts as the magnet 108, may be formed of a ferromagnetic body such as iron and the like or of a magnetic body in place of the magnet 108. Further, an electric field may be applied in place of the magnetic field, and a charged body or a dielectric may be built in the capsule 103 and the like.

Note that embodiments and the like which are arranged by partly combining the respective embodiments described above also belong to the present invention.

In this invention, it is apparent that working modes different in a wide range can be formed on the basis of this invention without departing from the spirit and scope of the invention. This invention is not restricted by any specific embodiment except being limited by the appended claims.

What is claimed is:

1. A capsule endoscope system comprising:
a capsule endoscope body having an insert axis;
a magnet disposed in the capsule endoscope body having an N-pole offset from the insert axis in a first direction and an S-pole being offset from the insert axis in a second direction opposite to the first direction; and
a magnetic field generation device configured to generate a first magnetic field in a direction having lines of action parallel to the insert axis and a second magnetic field in an opposite direction having lines of action parallel to the insert axis and further configured to periodically change between the first magnetic field and the second magnetic field thereby acting on the N-pole and the S-pole so as to make the capsule endoscope body vibrate about an axis perpendicular to the insert axis.

2. The capsule endoscope system according to claim 1, wherein the magnetic field generation device is configured such that the lines of action of the first and second magnetic fields generated by the magnetic field generation device rotate about the insert axis acting as a center axis.

3. The capsule endoscope system according to claim 1, comprising:
a thrust generating portion for generating a thrust in the direction of the insert axis.

4. The capsule endoscope system according to claim 1, wherein the magnet is a center of gravity.

5. The capsule endoscope system according to claim 1, wherein the magnetic has a single magnetized direction.

6. The capsule endoscope system according to claim 5, wherein
the magnet is disposed such that a center in a longitudinal direction of the magnet is positioned at a center in an axis direction of the insert portion, and
N and S poles respectively at both ends of the magnetized direction generate couples when applied with a magnetic field in the axis direction.

7. A medical apparatus comprising:
a capsule endoscope having a main body for insertion into a body cavity, the main body having an approximately cylindrical outside shape;
a magnet disposed in the main body having an N-pole offset from a cylindrical axis of the capsule endoscope body in a first direction and an S-pole being offset from the cylindrical axis in a second direction opposite to the first direction;
a spiral structure disposed around a side of the main body of the capsule endoscope;
a thrust generation mechanism having a rotation drive means for rotating the spiral structure about the cylindrical axis of the main body and generating a thrust in the direction of the cylindrical axis; and
a magnetic field generation device configured to generate a first magnetic field in a direction having lines of action in parallel with the cylindrical axis and a second magnetic field in an opposite direction having lines of action parallel to the cylindrical axis and further configured to periodically change between the first magnetic field and the second magnetic field thereby acting on the N-pole and the S-pole so a to make the main body of the capsule endoscope vibrate about an axis perpendicular to the cylindrical axis.

8. The medical apparatus according to claim 7, wherein
the poles of the magnet, including N and S poles, are oriented in a single direction, and
the N and S poles at both ends in the single direction generate couples when the magnet is applied with a magnetic field in an axis direction of the insert portion.

9. A medical apparatus guide system for guiding a medical apparatus into a body cavity comprising:
a rotation magnetic field generation device for generating a rotation magnetic field;
a magnetic field generation device for generating a magnetic field in a direction perpendicular to the rotation plane of the rotation magnetic field;
a medical apparatus main body having an insert portion inserted into the body cavity;
a thrust generation structure disposed to the medical apparatus main body; and
a magnet fixed to the medical apparatus main body with a magnetic pole direction facing a direction perpendicular to the thrust generating direction of the thrust generation structure,
wherein the magnet has an N-pole in a first direction and an S-pole in a second direction opposite to the first direction, and
wherein the magnetic field generation device is configured to generate first and second magnetic fields perpendicular to the rotation plane of the rotation magnetic field and in opposite directions, respectively, to generate lines of action parallel to the perpendicular direction in the medical apparatus main body and further configured to periodically change between the first magnetic field and the second magnetic field thereby acting on the N-pole and the S-pole so as to make the medical apparatus main body vibrate about an axis perpendicular to the thrust generating device.

10. The medical apparatus guide system according to claim 9, wherein the thrust generation structure is a spiral structure disposed around the outer periphery of the medical apparatus main body.

11. The medical apparatus guide system according to claim 9, wherein a magnetic field in a direction perpendicular to the rotation plane of the rotation magnetic field is an alternate current magnetic field.

12. The medical apparatus guide system according to claim 11, wherein a magnetic field in a direction perpendicular to the rotation plane of the rotation magnetic field is an alternate current magnetic field, and the frequency thereof is 2 Hz or more to 10 Hz or less.

13. The medical apparatus guide system according to claim 11, wherein the, frequency of the alternate current magnetic field in the direction perpendicular to the rotation plane of the rotation magnetic field is higher than the rotation frequency of the rotation magnetic field.

14. The medical apparatus guide system according to claim 11, wherein the frequency of the alternate current magnetic field in the direction perpendicular to the rotation plane of the rotation magnetic field is two times to ten times higher than the rotation frequency of the rotation magnetic field.

15. The medical apparatus guide system according to claim 9 comprising:

magnetic field control means for controlling the magnetic field generation device.

16. The medical apparatus guide system according to claim 15, wherein the magnetic field control means has a function for switching presence or absence of the magnetic field in the direction perpendicular to the rotation plane of the rotation magnetic field.

17. The medical apparatus guide system according to claim 15, wherein the magnetic field control means has a function for making the strength of the magnetic field in the direction perpendicular to the rotation plane of the rotation magnetic field variable.

18. The medical apparatus guide system according to claim 15, wherein the magnetic field control means has a function for making the frequency of the magnetic field in the direction perpendicular to the rotation plane of the rotation magnetic field variable.

19. The medical apparatus guide system according to claim 9, wherein the magnetic field strength of the magnetic field in the direction perpendicular to the rotation plane of the rotation magnetic field is smaller than the magnetic field strength of the rotation magnetic field.

20. The medical apparatus guide system according to claim 9, further comprising a storage portion for storing information on the rotation magnetic field.

* * * * *